US010463626B2

(12) United States Patent
Prestidge et al.

(10) Patent No.: US 10,463,626 B2
(45) Date of Patent: Nov. 5, 2019

(54) DRUG DELIVERY COMPOSITION COMPRISING POLYMER-LIPID HYBRID MICROPARTICLES

(71) Applicant: UNIVERSITY OF SOUTH AUSTRALIA, Adelaide, South Australia (AU)

(72) Inventors: Clive Allan Prestidge, Semaphore South (AU); Paul Matthew Joyce, Hope Valley (AU)

(73) Assignee: University of South Australia (AU)

( * ) Notice: Subject to any disclaimer, the term of this patent is extended or adjusted under 35 U.S.C. 154(b) by 0 days.

(21) Appl. No.: 15/556,913

(22) PCT Filed: Mar. 11, 2016

(86) PCT No.: PCT/AU2016/000080
§ 371 (c)(1),
(2) Date: Sep. 8, 2017

(87) PCT Pub. No.: WO2016/141413
PCT Pub. Date: Sep. 15, 2016

(65) Prior Publication Data
US 2018/0092854 A1 Apr. 5, 2018

(30) Foreign Application Priority Data
Mar. 11, 2015 (AU) ................. 2015900861

(51) Int. Cl.
A61K 9/50 (2006.01)
A61K 31/495 (2006.01)
(52) U.S. Cl.
CPC .......... A61K 9/5031 (2013.01); A61K 9/5015 (2013.01); A61K 9/5089 (2013.01); A61K 31/495 (2013.01)

(58) Field of Classification Search
CPC .. A61K 9/5015; A61K 31/495; A61K 9/5089; A61K 9/5031
See application file for complete search history.

(56) References Cited

U.S. PATENT DOCUMENTS

2004/0096515 A1 5/2004 Bausch et al.
2009/0263486 A1* 10/2009 Prestidge ............... A61K 9/501
424/489

FOREIGN PATENT DOCUMENTS

WO WO 2006/130904 A1 12/2006
WO WO 2007/128066 A1 11/2007
(Continued)

OTHER PUBLICATIONS

International Search Report and Written Opinion prepared by the Australian Patent Office dated Jun. 2, 2016, for International Application No. PCT/AU2016/000080.
(Continued)

Primary Examiner — Jianfeng Song
(74) Attorney, Agent, or Firm — Sheridan Ross P.C.

(57) ABSTRACT

A dry composition, comprising three-dimensional porous microparticles, wherein the microparticles comprise: (i) an active substance (eg a poorly water soluble drug), (ii) polymeric nanoparticles such as those composed of a biocompatible and/or biodegradable polymer (eg a PLGA polymer) (iii) lipid droplets (eg droplets of a medium chain triglyceride (MCT)), (iv) a nanoparticle stabilizing agent such as PVA or DMAB, and optionally, (v) a cryoprotectant (eg mannitol); wherein said active substance is carried by said nanoparticles and/or lipid droplets. The composition of the present invention may be formulated into, for example, a medicament for the treatment and/or prevention of various diseases or disorders (eg human or veterinary therapeutics). The average diameter of the individual microparticles of the (Continued)

composition, may be in the order of 2.5-3.5 μm which are particularly suitable for administration to the lung.

10 Claims, 9 Drawing Sheets

(56)     References Cited

FOREIGN PATENT DOCUMENTS

| | | |
|---|---|---|
| WO | WO 2008/128292 A1 | 10/2008 |
| WO | WO 2009/037482 A2 | 3/2009 |

OTHER PUBLICATIONS

Dinsmore A.D. et al., "Colloidosomes: Selectively Permeable Capsules Composed of Colloidal Particles", Science, 2002, vol. 298, pp. 1006-1009.

Whitby C.P. et al., "Poly(lactic-co-glycolic acid) as a particulate emulsifier", Journal of Colloid and Interface Science, 2012, vol. 375, pp. 142-147.

Sengel Turk C.T. et al., "Preparation of polymeric nanoparticles using different stabilizing agents", J. Fac. Pharm, Ankara, 2009, vol. 38, No. 4, pp. 257-268.

Yasmin R. et al. "Lyophilized Silica Lipid Hybrid (SLH) Carriers for Poorly Water-Soluble Drugs: Physicochemical and In Vitro Pharmaceutical Investigations", Journal of Pharmaceutical Sciences, 2014, vol. 103, pp. 2950-2959.

Joyce P. et al., "Bioactive Hybrid Particles from Poly(D,L-lactide-co-glycolide) Nanoparticle Stabilized Lipid Droplets", ACS Applied Materials & Interfaces, Jul. 16, 2015, vol. 7, pp. 17460-17470.

\* cited by examiner

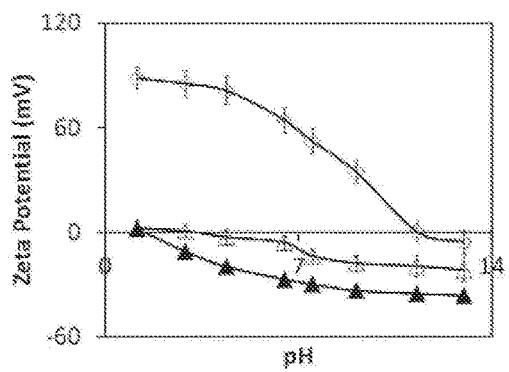
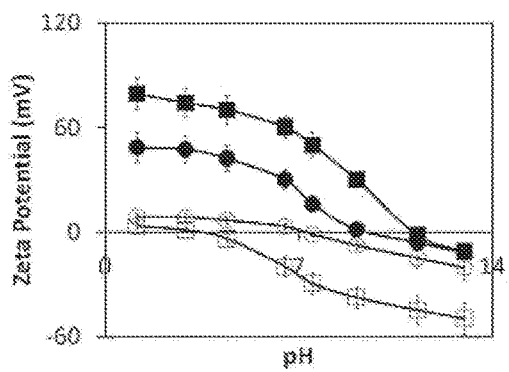
Figure 2A          Figure 2B
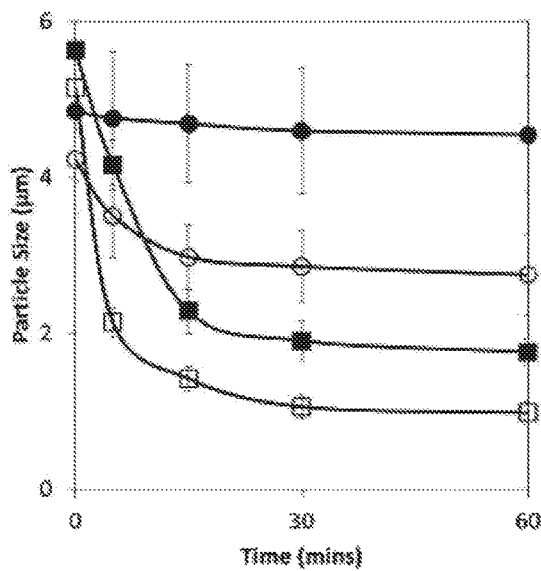
Figure 4

Figure 3

DRUG DELIVERY COMPOSITION COMPRISING POLYMER-LIPID HYBRID MICROPARTICLES

CROSS-REFERENCE TO RELATED APPLICATIONS

The present application is a national stage application under 35 U.S.C. 371 and claims the benefit of PCT Application No. PCT/AU2016/000080 having an international filing date of 11 Mar. 2016, which designated the United Sates, which PCT application claimed priority from Australian Provisional Patent Application No 2015900861 titled "Novel drug delivery composition" filed on 11 Mar. 2015, the disclosures of each of which are incorporated herein by reference in its entirety.

Technical Field

The present invention relates to a novel composition for the delivery of an active substance (eg a pharmaceutical agent such as a drug or other biologically active molecule including proteins and peptides) to a subject.

INCORPORATION REFERENCE

The following publications are referred to in the present specification and their contents are hereby incorporated by reference in their entirety:

Rao J P and K E Geckeler. Polymer nanoparticles: Preparation techniques and size control. *Prog Polym Sci* 36:887-913 (2011)[37]; and Makadia H K and S I Siegel. Poly. Lactic-co-Glycolic Acid (PLGA) as Biodegradable Controlled Drug Delivery Carrier. *Polymers* 3:1377-1397 (2011)[38].

BACKGROUND

A major challenge facing nanotechnology research is the development of smarter and more powerful carriers for the effective delivery of pharmaceutical agents. In particular, formulating complex pharmaceutical agents such as proteins, peptides and lipophilic molecules, with nanocarriers is often required so as to overcome physicochemical limitations and thereby attain the full pharmaceutical potential of the molecules [1]. To this end, lipid-based compositions (eg liposomes and solid lipid nanoparticles) which encapsulate pharmaceutical agents have been the most widely investigated and, indeed, some compositions of this type have been adopted in certain drug delivery applications (eg oral delivery of poorly water soluble drugs, anti-cancer formulations and vaccinations). However, even though lipid-based compositions can offer high levels of biocompatibility, favourable pharmacokinetic profiles and a relatively simple manufacture, to date the clinical use of such compositions has been somewhat limited due to instability, insufficient drug loading and/or characteristic "burst" release profiles of the encapsulated pharmaceutical agents [2-6].

An alternative approach to the formulation of pharmaceutical agents with nanocarriers involves the use of polymeric nanoparticles. Such nanoparticles have been investigated for use in the encapsulation of pharmaceutical agents with poor solubility and permeability, and have been found to provide higher levels of stability in biological fluid (ie. relative to lipid-based systems) while offering the possibility of a controlled rate of release of the pharmaceutical agent in a manner enabling effective drug delivery. However, the biocompatibility of many polymeric nanoparticles is not as high as lipid systems [7-9] and, consequently, considerable research effort has been devoted to engineering novel nanostructured carrier systems which might combine the advantages of lipid-based systems with those of polymeric nanoparticles, whilst minimising the physicochemical and biological limitations of the two nanocarriers.

A wide range of "hybrid" polymer-lipid nanocomposites have been recently reported which aim to address multifaceted drug delivery challenges [10-13, 45]. The most extensively fabricated type of hybrid particle consists of a lipid shell-polymer core architecture commonly assembled via a two-step method whereby anionic poly(D,L-lactide-co-glycolide) (PLGA) nanoparticles are mixed with cationic liposomes at a desired ratio [1, 14, 15]. However, single-step methods also exist which minimise batch-to-batch variation of physicochemical properties. Such methods utilise phospholipids as emulsifiers in the nanoparticle synthesis, resulting in the self-assembly of lipid-coated polymer nanoparticles [11, 16]. PLGA is an FDA-approved biodegradable polymer that has received the most extensive attention in the field of polymer-lipid hybrids due to its biocompatibility [17]. Lipid shell-polymer core morphology of PLGA-lipid hybrids have demonstrated several potential advantages over conventional delivery systems such as controllable particle size for high uptake, surface functionality for targeted delivery, high drug loading, entrapment of multiple pharmaceutical agents for combination therapies and "tunable" drug release profiles [12]. However, limitations are still present in such systems in regard to the stability of the lipid component and the burst release profiles from agents encapsulated within the lipid shell.

Previously, the present applicant developed a novel nanostructured lipid carrier system which consists of lipid encapsulated within a three-dimensional porous silica matrix or coacervate; providing silica-lipid hybrid (SLH) microparticles [18-20]. These SLH microparticles can be prepared by spray drying a silica-stabilised emulsion, with the water removal process inducing the aggregation of silica particles into a sponge-like matrix, whereby oil droplets are attached by lipophilic negatively or positively charged surfactants [21]. The surfactant charge impacts the nanostructure of the dry SLH microparticles due to the enhanced stabilising effect of nanoparticles when a charge neutralisation mechanism is operative in a Pickering emulsion [18]. The oral absorption of a number of lipophilic drugs has been shown to increase as a result of increased solubility in SLH microparticles, due to the enhanced and controlled digestion of lipid adsorbed in the three-dimensional silica matrix by the digestive enzyme, lipase [22-24]. The increased interfacial surface area of lipid, binding support of hydrophilic silica and reduced interference effect of digestion products have been shown to enhance lipase adsorption and action in SLH microparticles [25]. However, the exact effect of the surface chemistry of the solid matrix support on the digestibility of the encapsulated lipid is not well understood.

The ability to form hybrid microstructures with porous three-dimensional matrices whereby lipid is adsorbed may be controlled initially by the ability of solid nanoparticles to form a stable emulsion with medium chain triglycerides (MCT). PLGA nanoparticles with a slight negative surface charge, due to the use of PVA as a stabiliser, have shown the ability to impart kinetic stability to a range of non-polar oils by forming weak interactions with the oil-water interface [26]. Herein, the present applicant investigated whether the stabilising and controlled delivery characteristics of polymeric nanoparticles (such as PLGA nanoparticles) might be usefully combined with the solubilising effect of lipid droplets to form dry polymer (nanoparticle)-lipid hybrid (PLH) microparticles with a novel polymeric nanoparticle shell-lipid core architecture through the process of spray drying. Further, the present applicant investigated the use of a cryoprotectant (such as mannitol) in the spray drying step, and identified an additional form of dry PLH microparticles including the cryoprotectant (ie. polymer (nanoparticle)-lipid-cryoprotectant hybrid (PLCH) microparticles) with a novel architecture consisting of a three-dimensional matrix (or, in other words, coacervate) of the polymeric nanoparticles, lipid droplets and cryoprotectant.

SUMMARY

In a first aspect, the present invention provides a dry composition comprising three-dimensional porous microparticles, wherein said microparticles comprise: (i) an active substance, (ii) polymeric nanoparticles, (iii) lipid droplets, (iv) a nanoparticle stabilising agent, and optionally, (v) a cryoprotectant; wherein said active substance is carried by said nanoparticles and/or lipid droplets.

Typically, the active substance is a pharmaceutical agent such as a drug (particularly, a poorly water soluble drug) or other biologically active molecule (eg a protein such as an antibody or antibody fragment).

The polymeric nanoparticles preferably comprise a biocompatible and/or biodegradable polymer such as a PLGA polymer.

The lipid droplets preferably comprise a medium chain triglyceride (MCT).

The nanoparticle stabilising agent is preferably selected from poly vinyl alcohol (PVA) and didodecyldimethyl ammonium bromide (DMAB).

The optional cryoprotectant may be selected from mannitol, maltodextrin, lactose, trehalose, sucrose, glucose, fructose and sorbitol.

The microparticles of the composition preferably do not consist of a lipid shell-polymer nanoparticle core architecture like that seen in previously described hybrid polymer-lipid nanocomposites [1, 14, 15].

Preferably, the composition of the present invention is produced by a method comprising spray drying an oil in water (o/w) emulsion comprising lipid droplets and polymeric nanoparticles in the aqueous phase.

In a second aspect, the present invention provides a method for administering an active substance to a subject, wherein said method comprises administering to said subject a composition according to the first aspect.

The composition may be formulated into a medicament for oral, nasal, pulmonary, intra-muscular or subcutaneous administration to the subject.

In a third aspect, the present invention provides a method for producing a composition according to the first aspect, wherein said method comprises spray drying an emulsion comprising lipid droplets and polymeric nanoparticles in the aqueous phase.

In an embodiment of the method of the third aspect, the method comprises providing the emulsion comprising lipid droplets and polymeric nanoparticles in an aqueous phase, and thereafter removing the aqueous phase by spray drying.

BRIEF DESCRIPTION OF THE FIGURES

FIG. 2 provides graphical results showing: (A) Zeta potential as a function of pH for (◇) PLGA-1 nanoparticles, (△) PLGA-2 nanoparticles and (▲) a submicron emulsion stabilised with lecithin, on the addition of 10 mM NaCl; and (B) Zeta potential as a function of pH for (■) PLMH-1, (●) PLH-1, (○) PLMH-2 and (□) PLH-2 microparticle dispersions, on the addition of 10 nM NaCl;

Figure 3:
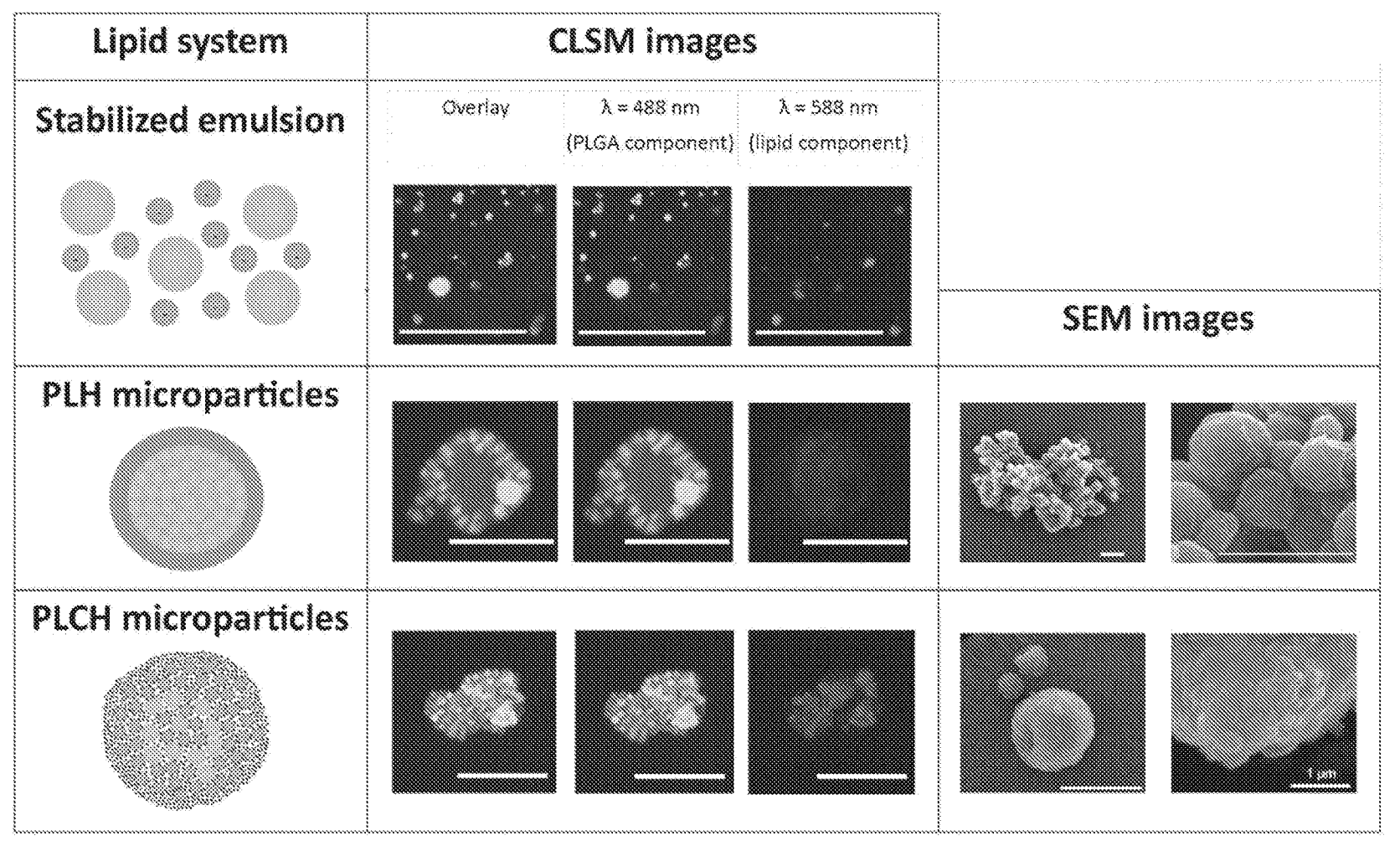

FIG. 3 provides confocal laser scanning microscopy (CLSM) cross section images and scanning electron micrograph (SEM) images demonstrating the differences in surface morphology and aggregation properties for PLH-1 (A and B) and PLMH-1 microparticles. The SEM images show: (A) A large aggregate of individual PLH microparticles, (B) up-close image demonstrating the surface morphology of PLH microparticles, (C) minimal aggregation of PLCH microparticles, and (D) up-close image demonstrating the surface morphology of PLCH microparticles;

FIG. 4 provides graphical results illustrating the reconstitution properties of (●) PLH-1, (○) PLH1-2, (■) PLMH-1 and (□) PLMH-2 microparticles, with mixing in digestion media over a 60-minute time period;

DETAILED DESCRIPTION

Figure 1:
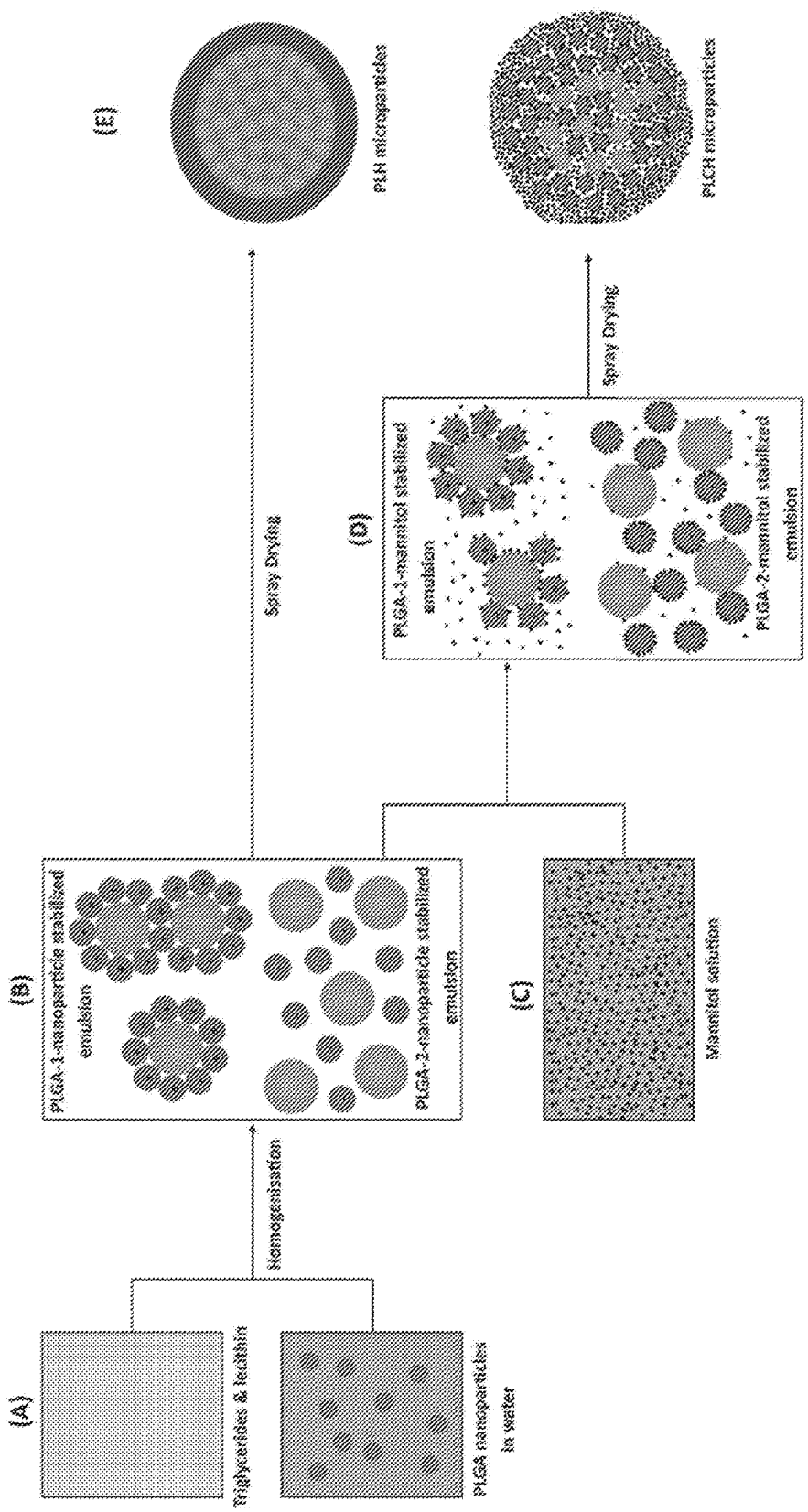
FIG. 1 provides a schematic representation of a two-step fabrication method of polymer-lipid hybrid (PLH) microparticles according to the present invention. (A) Oil phase: MCT (10 wt %) with dissolved anionic emulsifier, lecithin (0.6 wt %) and PLGA nanoparticies (80 wt % relative to oil) prepared by emulsion-diffusion-evaporation are dispersed in water. (B) PLGA-stabilised emulsion is formed (nb. positively charged PLGA nanoparticles coat negatively charged lipid droplets and negatively charged PLGA nanoparticles weakly cover lipid droplets due to electrostatics). (C) Mannitol solution (20 wt % relative to PLGA nanoparticles) is dispersed in the emulsion. (D) PLGA-mannitol stabilised emulsion is formed; coating of negatively charged PLGA nanoparticles on emulsion interface increases due to increase in zeta potential. (E) The emulsion is spray dried to form dry PLH and PLCH microparticles in the absence and presence of mannitol, respectively.

Novel microparticles comprising polymer nanoparticles and lipid were prepared by spray drying polymer (eg PLGA) nanoparticle-stabilised lipid emulsions. The resultant hybrid microparticles demonstrated three-dimensional porous properties (ie including internal proposity) enabling their use in, for example, compositions for the delivery of an active substance (eg a pharmaceutical agent such as a drug or other biologically active molecule) to a subject. By including a cryoprotectant (eg mannitol) in the emulsion prior to spray drying, the three-dimensional porous properties were able to be increased inasmuch as the internal porosity of the microparticles was increased.

In a first aspect, the present invention provides a dry composition comprising three-dimensional porous microparticles, wherein said microparticles comprise: (i) an active substance, (ii) polymeric nanoparticles, (iii) lipid droplets, (iv) a nanoparticle stabilising agent, and optionally, (v) a cryoprotectant; wherein said active substance is carried by said nanoparticles and/or lipid droplets.

The composition may comprise a dry substance comprising loose, aggregated and/or partially aggregated microparticles. By "dry composition", it is to be understood that the composition comprises less than about 10 weight percent (wt %) of water, more preferably less than about 5 wt %. As such, the composition will typically consist of a free flowing powder with no requirement for an anti-caking agent (eg calcium carbonate and powdered cellulose).

In the absence of a cryoprotectant, the microparticles will typically comprise an average diameter size in the range of 1 to 10 μm. However, preferably, the microparticles will comprise an average diameter size in the range of 2 to 5.5 μm. Using scanning electron microscopy (SEM), the individual microparticles typically have a smooth spherical morphology, while confocal laser scanning microscopy (CLSM) indicates that the microparticles consist of lipid droplets encapsulated within a solid outer shell of nanoparticles (see FIG. 1). These microparticles may be present in the composition in the form of large aggregates (eg with an average maximum dimension in the range of, for example, 20 to 100 μm). Hereinafter, microparticles lacking a cryoprotectant are referred to as polymer (nanoparticle)-lipid hybrid (PLH) microparticles.

In the presence of a cryoprotectant, the microparticles will also typically comprise an average diameter size in the range of 1 to 10 μm. However, in this case, the microparticles will preferably comprise an average diameter size in the range of 2 to 6 μm. Using scanning electron microscopy (SEM), the individual microparticles typically have a rough spherical morphology, while confocal laser scanning microscopy (CLSM) indicates that the microparticles consist of a three-dimensional matrix (or, in other words, a coacervate) of the polymer nanoparticles, lipid droplets and cryoprotectant (ie. with no polymer nanoparticle shell-lipid core architecture like that observed in the PLH microparticles). These microparticles may be present in the composition largely in the form of individual microparticles (ie. with minimal aggregation). Hereinafter, microparticles including a cryoprotectant are referred to as polymer (nanoparticle)-lipid-cryoprotectant hybrid (PLCH) microparticles. The redispersibility of PLCH microparticles (ie. to nanoparticles) appears to be significantly greater than that of PLH microparticles.

Therefore, microparticles according to the present invention do not consist of a lipid shell-polymer nanoparticle core architecture (ie. as seen in previously described hybrid polymer-lipid nanocomposites [1, 14, 15]).

The microparticles are porous, with an average pore size typically in the range of 25-500 mm. The internal porosity of PLCH microparticles appears to be more extensive than that of PLH microparticles.

The microparticles may be positively or negatively charged, or otherwise be neutral.

The active substance is carried in the composition by the polymeric nanoparticles and/or lipid droplets. By "carried", it is to be understood that the active substance may be dissolved within the polymeric nanoparticles and/or lipid droplets, and/or associated in another manner (eg the active substance may be wholly or partially adsorbed to the surface of the nanoparticles); such that the active substance may be released from the nanoparticles and/or lipid droplets (eg following degradation and/or diffusion).

The active substance may be selected from, for example, nutriceutical substances, cosmetic substances (including sunscreens and UV-absorbing molecules), pesticide compounds, agrochemicals and foodstuffs. However, more typically, the active substance is a pharmaceutical agent such as a drug or other biologically active molecule (eg a protein such as an antibody or antibody fragment, peptide such as an antigenic peptide of vaccine significance, or a nucleic acid molecule such as an antisense oligonucleotide or small interfering RNA (siRNA)).

The composition of the present invention may be particularly suitable for the delivery of a poorly water soluble (ie. lipophilic) drug to a subject. Poorly water soluble drugs are understood by those skilled in the art as compounds whereby low aqueous dissolution presents the major barrier to drug absorption across the gastrointestinal tract (GIT) into the blood. Consequently, the drug's oral bioavailability is limited.

The active substance may be a poorly soluble drug compound such as those of the group consisting, of:

anti-inflammatory agents including celecoxib (4-[5-(4-methylphenyl)-3-(trifluoromethyl) pyrazol-1-yl]benzenesulfonamide), indomethacin (1-(4-chlorobenzoyl)-5-methoxy-2-methyl-1-H-indole-3-acetic acid), valdecoxib (4-(5-methyl-3-phenylisoxazol-4-yl) benzenesulfonamide), meloxicam ((8E)-8-[hydroxy-[(5-methyl-1,3-thiazol-2-yl) amino]methylidene]-9-methyl-10,10-dioxo-10$\lambda^6$-thia-9-azabicyclo[4.4.0]deca-1,3,5-trien-7-one), rofecoxib (4-(4-methylsulfonylphenyl)-3-phenyl-5H-furan-2-one), diclofenac (2-(2-(2,6-dichlorophenylamino)phenyl)acetic acid), naproxen ((+)-(S)-2-(6-methoxynaphthalen-2-yl)propanoic acid) and combinations thereof;

anti-cancer agents such as paclitaxel, 7-Ethyl-10-hydroxy-camptothecin (SN 38), etoposide, taxotere, docetaxel, temozolomide and combinations thereof;

anti-emetic agents such as cinnarizine ((E)-1-(Diphenylmethyl)-4-(3-phenylprop-2-enyl)piperazine); vitamins and derivatives thereof including vitamin B, vitamin D, retinol (vitamin A) and retinoic acid; antibiotic agents including tetracycline, rifampacin, clarithromycin, erythromycin and combinations thereof;

anti-psychotic drugs including, ziprasidone, aripriprazole, etc., and cardiovascular drugs such as statins, etc.

The active substance, and particularly those that are poorly water soluble drugs, may be present in the composition within (and/or at the surface of) the polymeric nanoparticles and/or the lipid droplets. As a consequence, the composition enables the possible two phase release of a drug (eg the drug may be initially released from the polymeric nanoparticles in a first phase and thereafter released from the lipid droplets in a second phase, or vice versa), or the release of two different drugs (eg in a combination therapy). In one example of a composition for use in a combination therapy, the first active substance may be celecoxib present within (and/or at the surface of) the polymeric nanoparticles, and the second active substance is an anti-cancer agent (such as taxotere, docetaxel and temozolomide) dissolved within the lipid droplets.

Polymeric nanoparticles suitable for use in the composition of the present invention may be selected from those well known to those skilled in the art. Examples include those comprising: a polyester (eg poly(lactic) acid (PLA), poly (methyl methacrylate) (PMMA), polyacrylic acid (PAA), polyvinyl alcohol (PVA) and the like); a polyamide (eg poly-paraphenylene terephthalamide and poly[imino(1,6-dioxohexamethylene) iminohexamethylene); a co-polymer (eg poly(lactide)-block-poly(ethylene oxide)-block-poly (lactide) (PEO-PLA); and mixtures thereof. Other suitable polymeric nanoparticles, and their methods of preparation, are described by Rao and Geckeler [37] such as poly (oxyethylene glycol) polymer (POP), poly(ethylene glycol)-poly(lactide) (PEG-PLA), polycaprolactone (PCL), and polystyrene (PS) copolymer; the entire disclosure of Rao and Geckeler [37] is incorporated herein by reference.

Preferably, the polymeric nanoparticles will be biocompatible and/or biodegradable. By the term "biocompatible", those skilled in the art will understand that the nanoparticles, when administered to a subject, will not produce any substantial adverse effect [41]. By the term "biodegradable", those skilled in the art will understand that the nanoparticles, when administered to a subject, are broken down (ie. degraded) by hydrolysis and/or enzymatic processes within the body [41]. As such, the polymeric nanoparticles may be preferably selected from PLA, PLG, PLGA, PCL, chitosan, chitin, gelatin, polycyanoacrylate (PCA) and poly-alkyl-cyanoacrylate (PACA) polymers. However, most preferably, the polymeric nanoparticles comprise a PLGA polymer.

Due to its biocompatibility and biodegradability, PLGA polymers have been widely used to produce materials for introduction into a subject, such as drug delivery devices and tissue engineering scaffolds 1381. PLGA also has "tunable mechanical properties" (eg by controlling relevant parameters such as polymer molecular weight, lactide to glycolide ratio, and drug concentration, it is possible to control drug dosage and release profile from a PLGA carrier) and, as mentioned above, is FDA approved [38]; the PLGA polymers being biodegradable into biocompatible degradation products. In particular, PLGA is degraded into lactic and glycolic acids by hydrolysis (and possibly some enzymatic action [38]). In turn, the lactic acids enter the tricarboxylic acid cycle and are metabolised and eventually eliminated from the body as carbon dioxide and water [39], while glycolic acid is believed to be excreted either unchanged in the kidney or, like the lactic acids, via the tricarboxylic acid cycle where it is metabolised and eventually eliminated from the body as carbon dioxide and water. Biodegradable PLGA polymers, suitable for the production of polymeric nanoparticles for use in the present invention, are reviewed by Makadia and Siegel [38], along with the methods of their synthesis and fabrication into, inter alia, PLGA polymeric nanoparticles, the entire disclosure of Makadia and Siegel [38] is incorporated herein by reference. Some particular examples include PLGA polymers with a poly lactic acid (PLA)/poly glycolic acid (PGA) ratio of 50:50, 65:35, 75:25 and 85:15. In addition, PLGA copolymers may also be suitable. For example, di-block PLGA/PEG co-polymers (PLGA-PEG) and tri-block PLGA/PEG/PLGA co-polymers may be suitable and may provide an added benefit of increased shelf stability [38].

With regard to PLGA polymers, typically, the higher the content of poly glycolic acid in the PLGA, the faster is the rate of degradation (eg PLGA 50:50 degrades faster than 65:35, which in turn degrades faster than 75:25 etc.)[38], as the hydrophilicity of the PLGA is increased with increasing PGA content (thereby resulting in quicker degradation by hydrolysis). Also, with the increasing hydrophilicity (and decreasing hydrophobicity), degradation of the lipid droplet content of the composition through lipolysis will reduce due to the inhibition of lipase. On the other hand, the use of a biodegradable polymer with higher molecular weight will generally exhibit a lower rate of degradation. The polymers used in the present invention, and particularly where a PLGA polymer is used, may have a molecular weight (MW) in the range of, fin example, 5-100 kDa, more preferably 25-75 kDa, and most preferably, 30-60 kDa. The ability to select PLGA polymers with different MW and/or PLA/PGA ratios enables "tuning" of the release profile of the active substance from the composition of the present invention. In addition, the use of a PLGA with a higher content of PGA may also assist in raising the glass transition temperature (tg), which can make the production of the composition of the present invention more amenable to a spray drying method [38]; although as discussed below, the inclusion of a cryoprotectant can enable the use of PLGA polymers with lower amounts of PGA (eg PLGA 75:25 and PLGA 85:15).

Most preferably, the polymeric nanoparticles of the composition of the present invention comprise a PLGA 50:50 polymer with a MW of 30-60 kDa.

The polymeric nanoparticles preferably have an average diameter in the range of 2-500 nm, more preferably 5-200 nm, and most preferably about 150 nm.

The composition of the present invention comprises lipid droplets, preferably droplets of a medium chain triglyceride (MCT), although droplets of a long chain triglyceride (LCT) can also be suitable. Those skilled in the art will understand that MCTs contain 6-12 carbon fatty acid esters of glycerol. Suitable examples of MCTs include caproic acid (C6:0), caprylic acid (C8:0), capric acid (C10:0) and lauric acid (C12:0), and mixtures thereof. A specific suitable example is Miglyol® 812 (Cremer GmbH & Co, Cincinnati, Ohio, United States of America) which consists of a mixture of caprylic triglyceride and capric triglyceride. Suitable LCTs include soybean oil and safflower oil. The lipid droplets may optionally comprise a standard emulsifier, preferably an anionic surfactant such as, for example, lecithin and sodium deoxycholate. Anionic surfactants induce a negative charge into the droplets.

The nanoparticle stabilising agent may be selected from any of those well known to those skilled in the art including sodium dodecyl sulphate (SDS), polyoxyethylene-polyoxypropylene block copolymer surfactant (Pluronic® F-68; Sigma-Aldrich Co, LLC, St Louis, Mo., United States of America), Pluronic® F-127 surfactant (Sigma-Aldrich Co. LLC), poloxamine, polyethylene glycol (PEG), poly lactic acid (PLA), polyethylene glycol sorbitan mortooleate (Tween® 80; Sigma-Aldrich Co. LLC) and Vitamin E TPGS (d-alpha tocopheryl polyethylene glycol 1000 succinate; Antares Health Products Inc., Batavia, Ill., United States of America). However, preferred stabilising agents include poly vinyl alcohol (PVA) and didodecyldimethyl ammonium bromide (DMAB). The stabilising agent is preferably present during the synthesis of the polymeric nanoparticles, in which case, the stabilising agent may confer a charge on the nanoparticle surface. For example, the presence of PVA during the synthesis of PLGA nanoparticles produces a negative charge whereas the presence of DMAB during the synthesis of PLG nanoparticles produces a positive charge that coats the nanoparticle. When used in the composition with negatively charged lipid droplets (eg lecithin-stabilised lipid droplets), such positively charged PLGA nanoparticles will be caused to electrostatically coat the lipid droplet surface and thereby increase the stability of the three-dimensional structure of the porous microparticles in the dry composition.

The optional cryoprotectant may be selected from any of those well known to those skilled in the art. However, preferred cryoprotectants include mannitol, maltodextrin, lactose, trehalose, sucrose, glucose, fructose and sorbitol.

The composition of the present invention may comprise: 0.01 to 20 wt % of the active substance (preferably, 1-5 wt %), 10 to 60 wt % of the polymeric nanoparticles (preferably, 25-50 wt %), 5 to 50 wt % of lipid droplets (preferably, 25-50 wt %), 1 to 40 wt % of the nanoparticle stabilising agent (preferably, 10-25 wt %), and 0 to 17.5 wt % of the cryoprotectant (preferably, 0-10 wt %); wherein the wt % amounts are based on the total weight of the composition.

Where an emulsifier is used to stabilise the lipid droplets, the emulsifier may be present in an amount of 0.01 to 2.5 wt % based on the total weight of the composition.

While the active substance may be present in the composition in an amount in the range of 0.01 to 20 wt %, it will be understood by those skilled in the art that the actual amount present may vary considerably depending upon, for example, the particular components of the composition, the solubility of the particular active substance (which can often be increased by the presence of an emulsifier) and the manner of release of the active substance that is desired.

With an increasing amount of polymer nanoparticles, the rate of degradation of the lipid droplets through lipolysis by lipase will decrease.

The composition of the present invention may be produced by, for example, spray drying, freeze drying and fluidised bed procedures.

Preferably, the composition of the present invention is produced by a method comprising spray drying an oil in water (o/w) emulsion comprising lipid emulsion droplets and polymeric nanoparticles to the aqueous phase. The polymeric nanoparticles in the aqueous phase may have a stabilising effect on the lipid droplets. The spray drying will preferably be conducted at a temperature less than the tg of the biocompatible polymer (eg less than 60° C., for PLGA). At temperatures greater than the tg of the polymer, the polymeric nanoparticles will disintegrate and agglomerate during the spray drying process. Other spray drying parameters, such as emulsion flow rate and air flow rate, are preferably set to provide a high level or optimal level of removal of residual moisture (eg an emulsion flow rate <1 mL/min, such as for example, a flow rate in the range of 0.25 to 0.75 mL/min, and an air flow rate <1 m$^3$/min, such as for example, a flow rate in the range of 0.25 to 0.75 m$^3$/min). With PLGA nanoparticles, the emulsion flow rate may preferably be about 0.5 m$^3$/min, and the air flow rate may preferably be about 0.6 m$^3$/min.

More preferably, the composition of the present invention is produced by a two-step method of providing an o/w emulsion comprising lipid droplets stabilised by polymeric nanoparticles in an aqueous phase, and thereafter removing the aqueous phase by spray drying. The emulsion may be produced by homogenising a mixture comprising lipid in an aqueous dispersion of polymeric nanoparticles. The active substance is preferably present in the mixture. The active substance may be included in the polymer preparation for nanoparticle production (ie. such that the active substance is carried by the nanoparticles).

The emulsion may comprise a standard emulsifier, preferably an anionic surfactant such as lecithin. The emulsifier may be present in an amount of 0.1 to 5 wt %, preferably about 0.5 to 2 wt %, of the weight of the lipid droplets. The amount of polymeric nanoparticles present in the emulsion may be up to 80 wt % relative to the weight of the lipid emulsion droplets. The emulsion may optionally include a cryoprotectant (eg mannitol). The cryoprotectant may be present in an amount in the range of about 1 to 35 wt %, preferably 10 to 20 wt %, relative to the weight of the polymeric nanoparticles.

The average diameter of the individual microparticles of the composition will typically be in the range of 1-20 μm, preferably 2-10 μm, and most preferably <5 μm (for example, in the order of 1 to 4 μm or 2.5-3.5 μm). Microparticles of this size are suitable for a wide range of uses. In terms of therapeutic uses, microparticles of this size are particularly suitable for administration to the lung. That is, studies have shown that microparticles <5 μm, particularly in the order of 2.5-3.5 μm have the best level of penetration and retention in the lung, even when the subject is experiencing airflow obstruction (eg associated with mild to moderate asthma)[40]. In contrast, microparticles >5 μm have a tendency to get "stuck at the back of the throat" or, in other words, the oropharynx, while sub-micron particles (ie particles <1 µm) are not readily retained in the lung (ie they exit upon exhalation).

The composition of the present invention may be formulated into, for example, a medicament for the treatment and/or prevention of various diseases or disorders (eg human or veterinary therapeutics). The medicament may be suitable for, for example, oral administration, delivery to the mucous membranes (eg nasal and/or pulmonary administration) or subcutaneous administration. For oral administration, the medicament may be in the form of any suitable oral dosage form including tablets, caplets, capsules, liquid emulsions and suspensions and elixirs. For nasal and/or pulmonary delivery, the medicament may be provided in the form of a dry powder for a dry powder inhaler device (eg a device well known to those skilled in the art which, typically, produce a drug aerosol by directing turbulent air through loose powder). For subcutaneous administration, the composition may be formulated into a solid medicament suitable for implantation into the body by, for example, surgery. Alternatively, the composition may be formulated into a depot-forming composition that may be subcutaneously injected into the subject. Such solid and depot-forming implantable medicaments may be particularly suitable for long term requirements (eg where a sustained release of the active substance is desired).

In a second aspect, the present invention provides a method for administering an active substance to a subject, wherein said method comprises administering to said subject a composition according to the first aspect.

The composition may be formulated into a medicament for oral, nasal, pulmonary, intramuscular or subcutaneous administration to the subject.

Generally, the subject will be a human, typically an adult. However, the present invention may also be applicable to non-human subjects such as, for example, livestock (eg cattle, sheep and horses), exotic animals (eg tigers, lions, elephants and the like) and companion animals (such as dogs and cats).

In a third aspect, the present invention provides a method for producing a composition according to the first aspect, wherein said method comprises spray drying an oil in water (o/w) emulsion comprising lipid droplets and polymeric nanoparticles in the aqueous phase.

The polymeric nanoparticles in the aqueous phase may have a stabilising effect on the lipid droplets.

In an embodiment of the method of the third aspect, the method comprises providing the o/w emulsion comprising lipid droplets and polymeric nanoparticles in an aqueous phase, and thereafter removing the aqueous phase by spray drying.

Again, the polymeric nanoparticles in the aqueous phase may have a stabilising effect on the lipid droplets.

The spray drying will preferably be conducted at a temperature less than the tg of the biocompatible polymer (eg less than 60° C. for PLGA).

The emulsion may be produced by homogenising a mixture comprising lipid in an aqueous dispersion of polymeric nanoparticles. The active substance is preferably present in the mixture. The active substance may be included in the polymer preparation for nanoparticle production (ie. such that the active substance is carried by the nanoparticles). The emulsion may be formed from an oil in water (o/w) emulsion comprising 1-70% (w/w) lipid in water, preferably, 1-25% (w/w), more preferably 5-20% (w/w), and most preferably about 10% lipid in water. The o/w emulsion may comprise a suitable amount of a standard emulsifier, preferably an anionic surfactant such as lecithin, such as 0.1 to 5 wt % (relative to the amount of the lipid) or, more preferably, about 0.5-2 wt %. The amount of polymeric nanoparticles present in the emulsion may be up to 80 wt % relative to the weight of the lipid droplets. The emulsion may optionally include a cryoprotectant (eg mannitol). The cryoprotectant may be present in an amount in the range of about 1 to 35 wt %, preferably 10 to 20 wt %, relative to the weight of the polymeric nanoparticles.

In a further aspect, the present invention provides an aqueous preparation for producing a composition according to the first aspect, wherein said preparation comprises: (i) an active substance, (ii) polymeric nanoparticles, (iii) lipid, (iv) a nanoparticle stabilising agent, and optionally, (v) a cryoprotectant.

Such an aqueous preparation may be provided as, for example, a component of a kit, wherein said kit may further comprise instructions for spray drying the preparation to produce a composition according to the first aspect. In preparation for the spray drying, the aqueous preparation may be mixed (preferably homogenised) to form an emulsion of lipid droplets stabilised by the polymeric nanoparticles.

In a still further aspect, the present invention provides a spray-dried composition comprising three-dimensional porous microparticles, wherein said microparticles comprise: (i) an active substance, (ii) polymeric nanoparticles, (iii) lipid droplets, (iv) a nanoparticle stabilising agent, and optionally, (v) a cryoprotectant; wherein said active substance is carried by said nanoparticles and/or lipid droplets.

The invention is hereinafter described with reference to the following non-limiting example(s) and accompanying figures.

EXAMPLE(S)

Example 1

Bioactive Hybrid Particles from PLGA Nanoparticle-Stablised Lipid Droplets

Materials and Methods
Materials

Poly(D,L-lactide-co-glycolide) (PLGA; 50:50, MW=30000-60000 Da), didodecyldimethyl ammonium bromide (DMAB) and polyvinyl alcohol (PVA; MW=30000-70000 Da) were purchased from Sigma-Aldrich Pty Ltd (Castle Hill, NSW, Australia). Medium chain triglyceride (MCT: Miglyol® 812) was obtained from Hamilton Laboratories (Adelaide, SA, Australia), and soybean lecithin (containing >94% phosphatidycholinc and <2% triglycerides) from BDH Merck (Sydney, NSW, Australia). Ethyl Acetate (AR Grade) was obtained from Sigma Aldrich (Australia). Materials used for the lipolysis study, including sodium taurodcoxycholate (NaTDC) 99%, trizma maleate type X-E-α-lecithin (approximately 60% pure phosphatidylcholine, from dried egg yolk), porcine pancreatin extract (activity equivalent to 8×USP specification), calcium chloride dehydrate and sodium hydroxide pellets, were all purchased from Sigma-Aldrich (Australia).

Preparation of PLGA Nanoparticles

Nanoparticles were prepared by a modified emulsion-diffusion-evaporation method developed by Hariharan et al, [27]. The average diameter of the nanoparticles was about 180 nm, 500 mg PLGA (50:50) was dissolved in 25 mL ethyl, acetate at room temperature for 2 hours. The organic phase was then added to 50 of an aqueous phase containing DMAB (PLGA-1 nanoparticles) or PVA (PLGA-2 nanoparticles) as a stabiliser (250 mg in 50 mL, 0.5%, w/v). The resulting primary emulsion was stirred at 1000 rpm for 3 hours and subsequently homogenised at 15000 rpm for 5 minutes using a high-pressure homogeniser (Avestin® EmulsiFlex-C5 Homogeniser). Water was added with constant stirring to this nanoemulsion to facilitate diffusion and finally, evaporation of ethyl acetate, leading to the nanoprecipitation of nanoparticles.

Preparation of PLGA-Lipid Hybrid Microcapsules

PLH microparticles were prepared using a two-step method (ie. homogenisation followed by spray drying of PLGA nanoparticle-stabilised emulsions) developed by Tan el al, [19] and shown in FIG. 1. The initial o/w emulsions were prepared by dissolving 0.6% (w/w) lecithin in 10% (w/w) oil (Miglyol® 812) and Milli-Q water was added as the continuous phase. PLGA nanoparticles were dispersed in Milli-Q water, which contained 80% (wt relative to oil content) of nanoparticles. The coarse emulsion was tumbled for 12 hours after the addition of PLGA nanoparticles prior to being homogenised (Avestin® EmulsiFlex-05 Homogenizer; Avestin Inc., Ottawa, ON, Canada) under a pressure of 1000 bar fix 5 cycles. The PLGA nanoparticle-stabilised emulsion was then spray dried (Mini Spray Dryer B-290; BÜCHI Labortechnik AG, Flawil, Switzerland) to form PLH microparticles under the conditions given in Table 1.

TABLE 1

| Spray Drying Conditions | |
|---|---|
| Emulsion flow rate | 0.5 mL/min |
| Air flow rate | 0.6 m³/min |
| Inlet temperature | 60° C. |
| Outlet temperature | 35° C. |
| Aspirator setting | 10 |

Preparation of PLCH Microparticles

PLCH microparticles were prepared in a similar manner to that described above for PLH microparticles, although in this case a mannitol dispersion, containing 20% (wt relative to PLGA nanoparticles) mannitol, was added to the PLGA nanoparticle dispersion. This mixture was then added to the emulsion before homogenisation and spray dried following the method described above.

Physicochemical Characterisation of PLGA-Lipid Hybrid Microparticles

Scanning Electron Microscopy (SEM)—

The particle size and surface morphology of PLH microcapsules was examined by high resolution analytical scanning electron microscopy. SEM (Quanta 450; FEI, Hillsboro, Oreg., United States of America). Each sample was mounted on double-sided adhesive tape and sputter coated with a platinum layer prior to imaging.

Lipid Loading Content—

The lipid loading content of PLH microcapsules was determined by thermogravimetric analysis (TGA). The particles were heated at a scanning rate of 10° C./min from 20-550° C. under nitrogen purging; the lipid completely decomposed by 500° C. The amount of lipid loaded within the microcapsules could be determined by the weight loss within this temperature range, minus that corresponding to water moisture.

Dispersibility Study—

The reconstitution properties of PLHs were assessed based on changes in droplet size over a period of time as characterised by laser diffraction (DLS) using a Malvern Mastersizer and dynamic light scattering using a Malvern Zetasizer Nano, respectively (Malvern Instruments Inc., Malvern, United Kingdom). Each composition (5 mg/ml powder) was redispersed in lipid digestion medium following the method of king et al. [28].

In Vitro Lipolysis Studies

Preparation of Lipid Digestion Medium—

The lipid digestion medium was prepared according to the method adapted from Sek et al. [29]. The fasted state mixed micelles (i.e. phospholipid/bile salt (1.25 mM PC/5 mM NaTDC)), were prepared in the following sequence: egg lecithin was dissolved in chloroform (4 mL) followed by evaporation of chloroform under vacuum (Rotavapor R E, BÜCHI Labortechnik, Switzerland) to form a thin film of lecithin around the bottom of a 50 mL round-bottom flask; NaTDC and digestion buffer [50 mM Trizma maleate (pH 7.5), 150 nM NaCl, and 5 nM $CaCl_2.2H_2O$] was added and the mixture was stirred for ~12 h to produce a transparent (light yellow) micellar solution. Pancreatin extracts (containing pancreatic lipase, colipase and other non-specific lipolytic enzymes such as phospholipase $A_2$) were freshly prepared each day by stirring 1 g of porcine pancreatin powder in 5 mL of digestion buffer for 15 min, followed by centrifugation (at ~5000 rpm, 4° C.) for 20 mm. The supernatant phase was collected and stored on ice until use.

Lipid Digestion Kinetics Studies—

The progress of lipid digestion was monitored for 180 min by using a pH-stat titration unit (TIM854 Titration Manager, Radiometer, Copenhagen, Denmark) according to the lipolysis protocol as described by Sek et al [29]. Briefly, a known quantity of sample composition (equivalent to ~200 mg lipid) was dispersed in 18 mL of buffered micellar solution by stirring continuously for 10 min in a glass reaction vessel with thermostat (37° C.). The pH of the digestion medium was re-adjusted with 0.1 M NaOH or HCl to 7.50±0.01. Lipolysis was initiated by the addition of 2 mL of pancreatin extract (containing ~2000 TBU of pancreatic lipase activity) into the digestion medium. Free fatty acids (FFA) produced in the reaction vessel were immediately titrated with NaOH via an auto-burette to maintain a constant pH in the digestion medium at the pre-set value of 7.50±0.01 throughout the experiment. A solution of 0.6 M NaOH was used for long-chain lipids as per the established experiment protocol [29].

Results and Discussion

Formation of Hybrid Particles from PLGA Nanoparticle Stabilised Lipid Droplets

Nanocomposite microparticles consisting of PLGA nanoparticles and MCT droplets were prepared via a two-step fabrication method, whereby the oil-phase containing the anionic surfactant, lecithin, was homogenised with an aqueous dispersion of either positively or negatively charged PLGA nanoparticles. The consequent nanoparticle-stabilised emulsions were then spray dried, to form dry PLGA lipid hybrid (PLH) microparticles of 1-5 µm in size with a three-dimensional microstructure controlled by the interfacial structure of the precursor emulsions.

The PLGA nanoparticle charge was varied by using either DMAB or PVA as a stabiliser during the nanoparticle synthesis, in order to investigate the influence of emulsion stability on dry particle nanostructure. DMAB produced nanoparticles with a highly cationic charge, whereas PVA produced nanoparticles with an anionic charge due to the hydrolysis of poly(lactic acid) groups on the particle surfaces [30]. Lecithin induced negative charge onto the emulsion droplets causing oppositely charged PLGA-1 nanoparticles to electrostatically coat the lipid droplet interface. By contrast, negatively charged PLGA-2 nanoparticles required high nanoparticle concentrations to show droplet nanoparticle adsorption due to the electrostatic repulsion interactions between the two interfaces. Due to the high concentration of PLGA nanoparticles (80 wt % relative to oil concentration), the zeta potential of the stabilised emulsions and the dry PLH microparticles was dependent on the charge of the nanoparticle. Extrapolation of the data gives an isoelectric point between pH 9 and 10 for PLH-1 microparticles and pH 3 and 4 for PLH-2 microparticles (FIG. 2).

Figure 5A:
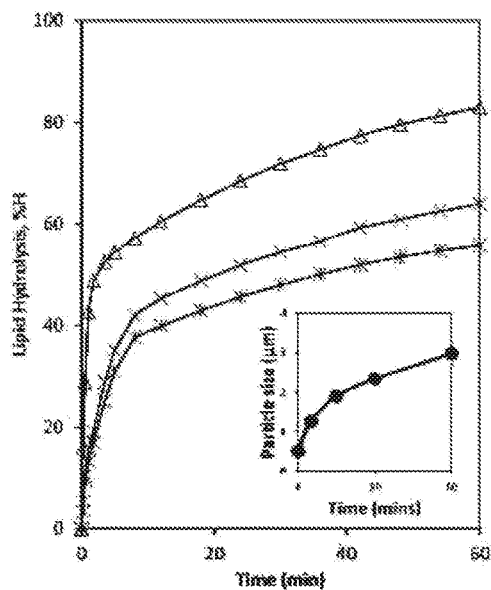
FIG. 5 provides graphical results showing the effect of (A) PLGA-1 nanoparticles and (B) PLGA-2 nanoparticles on the digestion profiles of submicron MCT emulsions when PLGA nanoparticles were added to the aqueous phase at (△) 0 wt %. (X) 10 wt % and (*) 50 wt %, relative to the lipid content in the emulsion systems. Inset; particle aggregation demonstrated for PLGA nanoparticles (50 wt %) and emulsion droplets by an increase in average particle size over a 60-minute period.
Figure 5B:
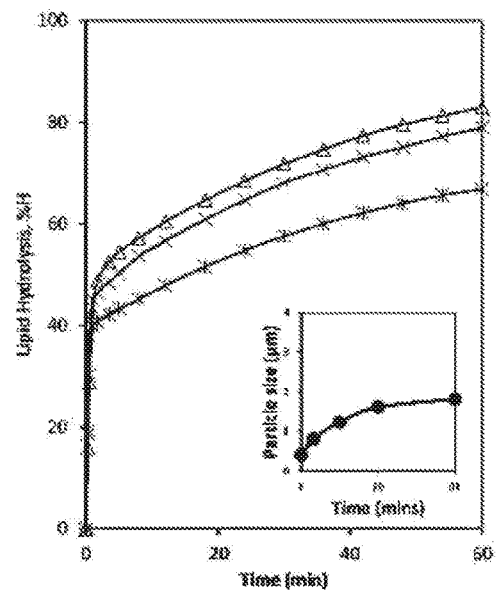

Spray dried stabilised emulsions of PLGA nanoparticles formed a cohesive and sticky solid material due to the aggregation of individual microparticles. This was independent of nanoparticle charge at 80 wt % PLGA relative to lipid, as it was demonstrated for both PLGA.-1 and PLGA-2 nanoparticles. Consequently, it was hypothesised that this was not due to emulsion stability but rather the high temperatures and shear forces of spray drying inducing cohesion between individual PLGA nanoparticles. Unlike other robust materials commonly used in spray drying, PLGA has a low glass transition temperature which introduces difficulties in maintaining the integrity of PLGA nanoparticles during this process. Carbohydrates, such as mannitol, act as bulking agents and provide protection to PLGA nanoparticles from shear forces and high temperatures during spray drying [31, 32]. As a result, mannitol was administered during the preparation method to investigate the effect of a carbohydrate cryoprotectant on the nanoparticle integrity and microparticle aggregation during the water removal step. The zeta potential, and particle size, increased for PLGA lipid-mannitol hybrid microparticles (Table 2) designated PLMH-1 and PLMH-2; yielding a pKa between 10 and 11 for PLMH-1 microparticles and 6 and 7 for PLMH-2 microparticles. Both positively and negatively charged nanoparticle-stabilised emulsions formed free flowing powders when spray dried with an aqueous solution of mannitol.

lighted in FIG. 4, whereby the reconstitution of PLCH microparticles into heterogeneous dispersions of PLGA nanoparticles and lipid droplets is demonstrated by the reduction of particle size over time from 5.63±1.2 μm to 1.76±0.3 μm and 5.15±1.0 μm to 0.98±0.2 μm for PLMH-1 microparticles and PLMH-2 microparticles, respectively. Minimal change in particle size was observed for PLH microparticles (4.85±0.9 μm to 4.55±0.75 μm and 4.23±0.7 μm to 2.75±0.51 μm for PLH-1 microparticles and PLH-2 microparticles, respectively) confirming that the PLGA nanoparticles were disrupted due to the high temperatures and shear stress of the water removal process, causing the nanoparticles to morph into a microcapsule-like structure whereby lipid is encapsulated within a solid PLGA outer shell (FIG. 1).

It was found that cationic PLGA nanoparticles exerted a greater level of stability on negatively charged lipid droplets due to strong electrostatic attraction, increasing the stability of the PLH microparticle three-dimensional structure in the dry composition. Thereby, the difference in PLMH-1 and PLMH-2 reconstitution can be attributed to the difference in electrostatic interactions between PLGA nanoparticles and emulsion droplets. Both PLH-2 and PLMH-2 experienced a greater rate and extent of particle redistribution than PLH-1 and PLMH-1, respectively, most likely due to the electrostatic repulsion between the PLGA-2 nanoparticles and lipid droplets. It is also hypothesised that the flocculation between cationic microparticles is greater than anionic microparticles due to the interaction between positively charge microparticles with small patches of negatively charged microparticle interface. This flocculation further reduced the redispersion of PLH-1 microparticles to primary nanoparticles and lipid droplets.

TABLE 2

| Sample | Stabiliser | Particle Size of PLGA NPs (nm) | Zeta Potential PLGA NPs[a] (mV) | Average particle size of hybrid microparticles (μm) | Zeta Potential of hybrid microparticles[a] (μm) | Lipid loading level (wt %) |
|---|---|---|---|---|---|---|
| PLH-1 | DMAB | 163.6 ± 8.1 | 90.5 ± 6.1 | 4.85 ± 0.9 | 16.2 ± 3.2 | 17 |
| PLH-2 | PVA | 256.8 ± 10.9 | −21.6 ± 3.6 | 4.23 ± 0.7 | −29.4 ± 6.4 | 14 |
| PLMH-1 | DMAB | 165.9 ± 7.4 | 90.5 ± 6.1 | 5.63 ± 1.2 | 49.9 ± 7.3 | 9 |
| PLMH-2 | PVA | 269.3 ± 12.4 | −21.6 ± 3.6 | 5.15 ± 1.6 | −1.2 ± 1.2 | 8 |

[a]The Zeta Potentials reported are in the pH range of 7.0-7.5.

SEM and CLSM images clearly showed that porous aggregates are formed for PLH microparticles in the size range of 20-100 μm, consisting of individual microparticles in the size range of 2-5.5 μm (FIG. 3). The difference in morphology and particle aggregation between individual PLH and PLCH microparticles was attributed to the addition of mannitol during the water removal process. Examination of SEM images of PLH microparticles demonstrates a smooth spherical morphology, with the absence of individual PLGA nanoparticles on the particle surface indicating that the nanoparticle integrity was not maintained during spray drying. In comparison, the inclusion of mannitol appears to increase the ability for the self-assembly of PLGA nanoparticles from the continuous phase to the droplet interface during spray drying, whilst maintaining the integrity of individual nanoparticles and forming a three dimensional porous structure whereby lipid droplets are encapsulated within a PLGA matrix. This is further high- In Vitro Lipid Digestion Studies Influence of PLGA Nanoparticles on Digestion of Lipid Droplets—

The effect of PLGA nanoparticles on lipid digestion was examined by assessing pancreatic lipase action in a stabilised emulsion system. In particular, different concentrations of PLGA-1 and PLGA-2 nanoparticles were added to a submicron MGT emulsion stabilised by lecithin to investigate this stabilising effect on lipid digestibility (FIG. 5). It was found that the initial rate of lipolysis was significantly reduced when emulsion droplets were stabilised with PLGA-1 nanoparticles, compared to PLGA-2 nanoparticles. This coincided with the enhanced ability for cationic nanoparticles (at pH 7.5) to stabilise and coagulate with anionic emulsion droplets (at pH 7.5) due to the electrostatic attraction between both interfaces. This is demonstrated in FIG. 5A inset, as the average particle size of the PLGA-1 stabilised emulsion increased 6-fold over a 60-minute period from 0.5±0.2 μm to 2.9±0.6 μm due to heterocoagulation between the nanoparticles and droplets, leading to physical shielding of the emulsion droplets and a reduced ability for lipase to adsorb to the lipid interface. PLGA-2 nanoparticles, however, carry a small negative charge at neutral pH and, consequently, electrostatic repulsive interactions between nanoparticles and emulsion droplets are believed to generate an energy barrier at close approach, restricting the number of nanoparticles that can weakly adsorb to the droplet interface through hydrophobic interactions, leading to less particle aggregation (0.4 μm to 1.82 μm over 60 minutes; FIG. 5B inset) than for the positively charged PLGA nanoparticles. A similar initial rate of digestion to that of a conventional submicron emulsion was observed for PLGA-2 nanoparticle-stabilised emulsions due to reduced physical shielding of the lipid by the nanoparticles, thereby allowing the enzyme to gain access to the lipid interface. However, as the lipid digestion proceeded for both PLGA-1 and PLGA-2 nanoparticles, emulsion droplets decreased in size, increasing the shielding effect of the PLGA nanoparticles and restricting the access of lipase to the oil-water interface, leading to reduced extents of lipolysis over a 60 minute period [22]. In both instances, as the concentration of nanoparticles increased from 10 wt % to 50 wt %, the rate and extent of digestion decreased due to increased physical shielding and steric hindrance. However, the degree of inhibition of lipase was significantly greater in PLGA-1 nanoparticles than in PLGA-2 nanoparticles due to the difference in nanoparticle charge. Thus, the overall extent of lipolysis for 10 wt % and 50 wt % PLGA-1 stabilised emulsions was 64.0±3.6% and 55.8±2.9%, respectively, compared to 78.9±5.6% and 66.9±5.1% for 10 wt % and 50 wt % PLGA-2 stabilised emulsions, respectively.

Digestion Kinetics for Spray Dried Hybrid Microparticles—

Figure 6:
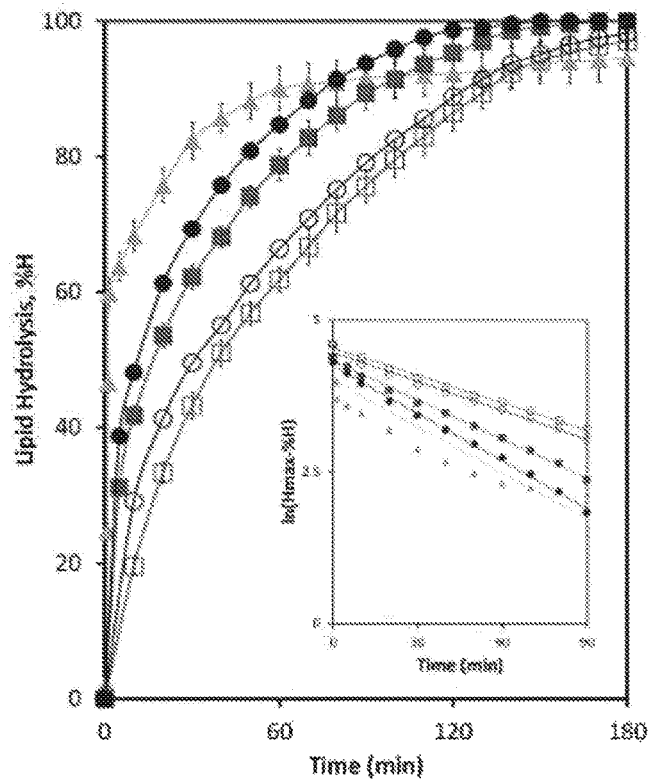
FIG. 6 provides graphical results showing, the lipase-mediated digestion kinetics for MCT in (□) PLH-1 microparticles, (○) PLH-2 microparticles, (■) PLMH-1 microparticles, (●) PLMH-2 microparticles and (▲) a submicron emulsion, under fasted state conditions over a 3-hour digestion period. Inset; the qualities of pseudo-first order fit.

FIG. 6 depicts the percent of lipid hydrolysis as a function of time for the four developed dry hybrid microparticles (ie. PLH-1, PLH-2, PLMH-1 and PLMH-2 microparticles) compared to a submicron MCT emulsion stabilised with lecithin. Under simulated fasted intestinal conditions, lipid digestion for the submicron emulsion occurred at a rapid initial rate due to a greater exposure of lipid substrate to lipase during the early phase of digestion before prompt inhibition at approximately 60% digestion. In comparison, lipolysis of all four hybrid microparticles occurred at a slower initial rate due to the steric hindrance of PLGA on enzyme adsorption but the overall extent of digestion was greater than for the submicron emulsion (100% for PLMH-1 and PLMH-2 microparticles versus 94.5±3.3% for submicron emulsion). Both the submicron emulsion and emulsion droplets within the dry microparticles were stabilised with lecithin. At low to moderate concentrations of lecithin, relative to lipid concentration, lecithin appears to enhance lipase action by removing the surface active digestion products from the emulsified interface. However, at high concentrations, or as the emulsion droplet sizes decreases, lecithin seems to interfere with lipase adsorption by competing with the enzyme for sites on the oil-water interface [33]. In addition to this, at insufficient bile salt concentrations, digestion products (ie. free fatty acids and monoglycerides) adsorb to the oil-water interface due to their amphiphilic structure, which further restricts lipase adsorption and inhibits lipolysis. The rapid decrease in emulsion droplet size and rapid release of digestion products from the submicron emulsion leads to an inhibition of enzymatic degradation due to a saturation of the oil-water interface. In comparison, a mechanism must exist for PLH and PLCH microparticles whereby lecithin and the released digestion products are removed from the pores, leaving a bare lipid interface for lipase adsorption and thereby facilitating complete digestion, it is hypothesised that the electrostatic interaction between the PLGA nanoparticles and negatively charged digestion products reduces the number of amphiphilic components that adsorb to the oil-water interface, and increases the level of vesicular and micellar structure formation [25].

Lipid hydrolysis of all dry hybrid microparticles demonstrated sustained digestion compared to PLGA nanoparticle-stabilised emulsions, indicating that there is a greater level of physical shielding of lipase by PLGA in the dry phase compared to the wet phase. The overall extent of lipolysis for PLH-1 microparticles was 61.8±3.7% over a 60-minute digestion period, which, was consistent with the enzymatic degradation of lipid for a 10 wt % PLGA-1 stabilised emulsion. Hence, the rate of lipid hydrolysis was significantly slower for PLH microparticles, but the overall extent of digestion was equal to a PLGA-stabilised emulsion. Slow initial digestion kinetics suggests slow adsorption of the enzyme from the aqueous continuous phase before becoming catalytically active at the interface [22], however, equivalent extent of digestion suggests that the microstructure facilitates sustained digestion and a reduced interference effect of digestion products and PLGA nanoparticles on lipase adsorption.

The hydrolysis of lipid encapsulated within PLH and PLCH microparticles showed pseudo-first order kinetics (FIG. 6 inset). In particular, the first order rate constants, k, were determined for each lipid system by fitting a curve to the ln(Hmax–H %) verses time (FIG. 6 inset) and are given in Table 3, along with the extent of hydrolysis after 3 hours digestion, $H_{max}$.

TABLE 3

| Lipid composition | Hydrolysis rate constant, k (min$^{-1}$ × 10$^{-2}$) | Extent of hydrolysis after 3 hours, $H_{max}$ |
|---|---|---|
| Coarse emulsion | 1.91 ($R^2$ = 0.98) | 94 ± 0.6 |
| Submicron emulsion | 30.5 ($R^2$ = 0.79) | 94 ± 3.3 |
| PLH-1 microparticles | 1.70 ($R^2$ = 0.96) | 97 ± 1.2 |
| PLH-2 microparticles | 2.43 ($R^2$ = 0.96) | 98 ± 1.9 |
| PLMH-1 microparticles | 3.69 ($R^2$ = 0.96) | 100 ± 0 |
| PLMH-2 microparticles | 4.87 ($R^2$ = 0.96) | 100 ± 0 |

Previous kinetic analysis demonstrated the inability to fit first-order kinetics to the digestion of a submicron emulsion as a result of the sharp decrease in reaction rate after 5 minutes of digestion, due to the role of amphiphilic compounds in inhibiting lipase adsorption as the emulsion droplet decreases in size [25]. Consequently, the first order rate constant of 0.305 min$^{-1}$ is significantly greater than those for the hybrid microparticles, but only describes the initial digestion kinetics. Along with this, digestion of lipid within silica-lipid hybrid (SLH) microparticles prepared according to Tan et al. [22] by spray drying silica nanoparticle-stabilised emulsion droplets, demonstrated tri-phasic pseudo-first order kinetics and thus required three first order rate constants to precisely describe the data. Digestion kinetics were enhanced in SLH microparticles compared to a submicron emulsion due to the increased surface area of lipid and the hydrophilic silica matrix facilitating the interfacial activation of lipase. The difference in digestion kinetics between the hybrid systems of silica and PLGA indicates that the change in surface chemistry and larger particle size of PLGA nanoparticles compared to silica alters the interaction between lipase and the lipid interface. While not to be bound by theory, it is considered that lipase adsorbs to the mostly hydrophobic PLGA surface in its inactive, "closed-lid" orientation, reducing the number of enzyme molecules available for catalysis and, thereby, reducing the lipid digestion rate. Further, the increased particle size that constitutes the solid matrix increases the steric hindrance of enzyme molecules to the lipid interface.

The digestion kinetics were enhanced when negatively charged PLGA-2 nanoparticles were used to prepare hybrid microparticles, both in the presence and absence of mannitol, when compared with positively charged PLGA-1 nanoparticles. The pseudo-first order rate constant increased from 0.017 and 0.037 $min^{-1}$ for positively charged PLH-1 and PLMH-1 microparticles, respectively, to 0.024 and 0.049 $min^{-1}$ for negatively charged PLH-2 and PLMH-2 microparticles, respectively (Table 3). This was consistent with previous studies that have demonstrated the effect of surface charge on digestion of conventional emulsion droplets; whereby, positively charged lipid droplets coagulate due to electrostatic interactions between the positively charged droplet interface and negatively charged digestion products that adsorb to the interface, reducing the accessible surface area for lipase adsorption [33, 34]. In addition to this, the rate and extent of lipolysis increased when mannitol was used in the composition.

Figure 7:
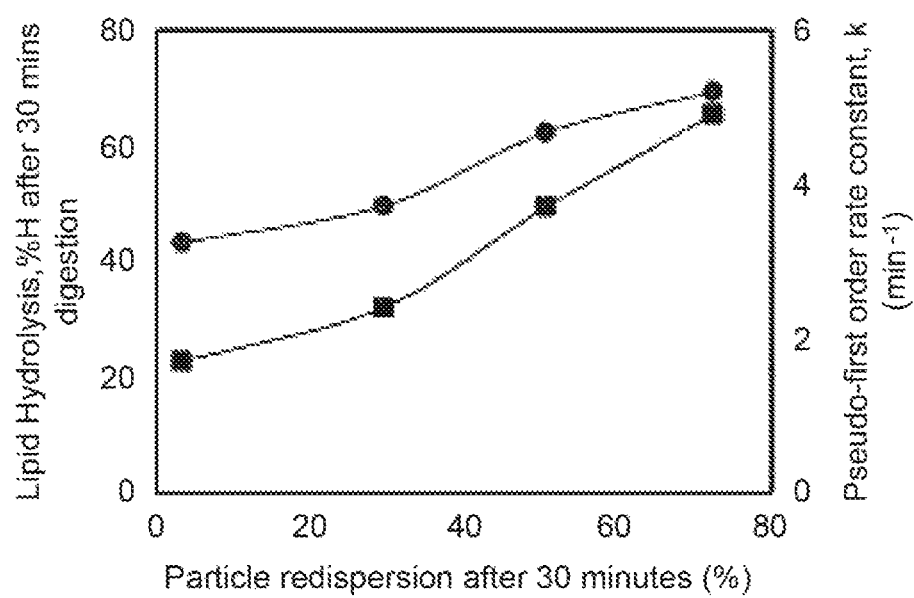
FIG. 7 provides graphical results showing the kinetics of lipolysis of microparticles according to the present invention as a function of the percent particle redispersion after 30 minutes agitation in digestion medium: extent of lipid hydrolysis after 30 min (circles, left axis) and the pseudo-first order rate constant, k (squares, right axis)
Figure 8:
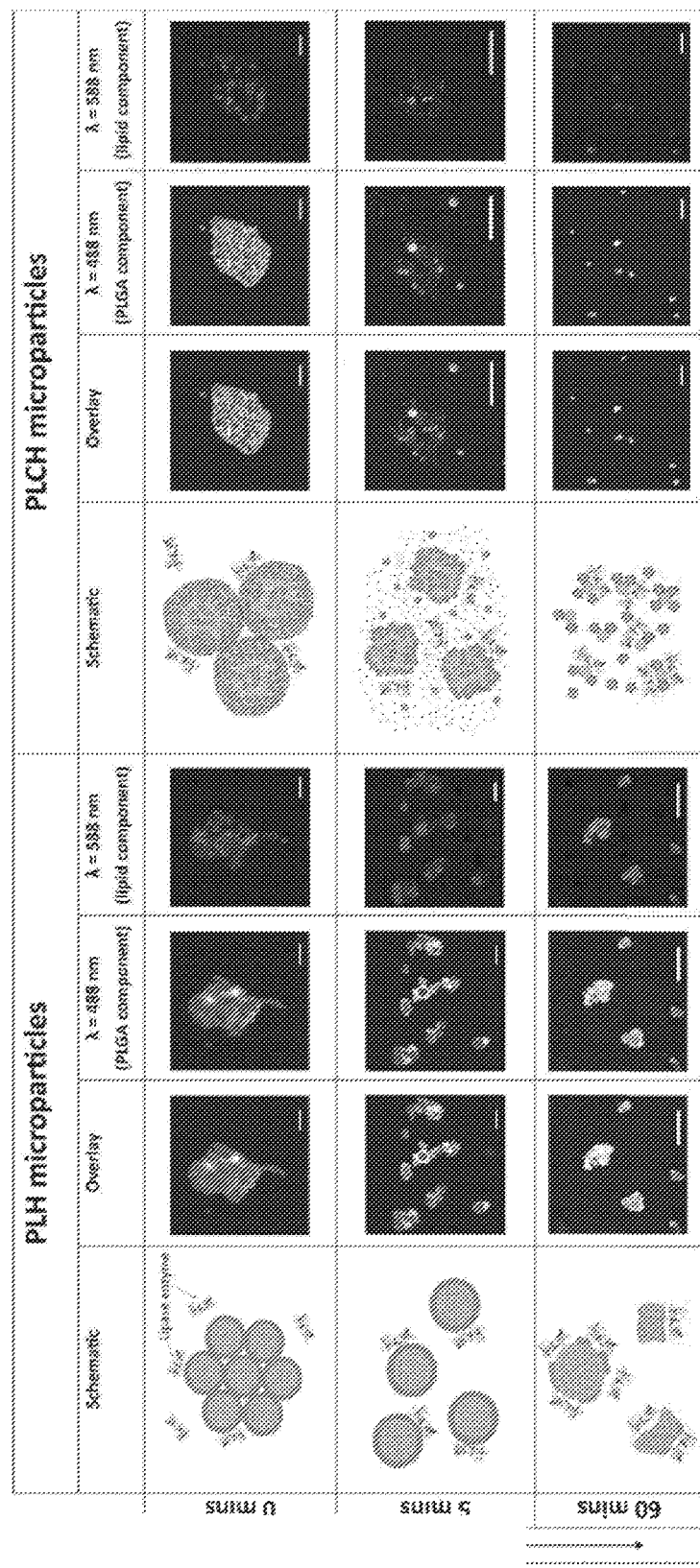
FIG. 8 provides CLSM cross section images and schematic representations of PLH and PLCH microparticles at 0, 5 and 60 minutes redispersion in digestion media. The degree of redispersion is clearly demonstrated to be greater in PLCH microparticles, compared to PLH microparticles, as the particle size and lipid content decreases significantly over time. Schematic representations: PLGA=mid grey, lipid=light grey, uniform circular droplet shape, mannitol=dark grey dots. Scale bars=10 μm.

The influence of surface charge and mannitol on the digestibility of lipid within the formulated hybrid microparticles is attributed to the effect that each component has on particle redispersibility. Thus, microparticle redispersibility was enhanced when PLGA nanoparticles were prepared with an anionic stabiliser and mannitol was administered as a cryoprotectant (FIG. 4). Attractive electrostatic interaction between positively charged PLGA nanoparticles and negatively charged lipid droplets appear to increase the stability of the microparticle structure causing a reduction in redispersion properties. Mannitol was found to act as a cryoprotectant during spray drying by maintaining the integrity of PLGA nanoparticles, thereby increasing the redispersion of microparticles to heterogeneous coagulations of PLGA nanoparticles and lipid droplets. The rate constant and extent of lipid digestion was linearly dependent on the microparticle redispersion/disintegration (FIG. 7), which is consistent with previous findings where the rate and extent was found to be linearly dependent on the surface area of lipid when adsorbed in porous silica [25]. That is, the lipid digestion is controlled by the ability for lipase to access the lipid interface [35, 36] and thereby, an increase in particle disintegration increases the accessible surface area of lipid, which in turn increases lipase adsorption (FIG. 8). The formation of heterogeneous dispersions of PLGA nanoparticles and emulsion droplets for PLCH microparticles increases the interfacial surface area of lipid, whereas the inability for PLH microparticles to redisperse due to the microcapsule-like structure (ie. where the microparticle consists of lipid droplets encapsulated within a solid outer shell of nanoparticles) restricts the number of lipase molecules that can bind to lipid interface, producing digestion kinetics similar to a coarse emulsion.

Whilst previously prepared PLGA-lipid hybrid microparticles with lipid shelf-polymer core architecture have demonstrated promising drug delivery applications, the novel three-dimensional porous structure of microparticles synthesised in this example address stability issues for the lipid component of hybrid microparticles. That is, by controlling lipase action through surface charge and cryoprotectant concentration, it is considered that this novel structure can facilitate controlled drug release and adsorption from the lipid component, in comparison to the common burst release mechanism of lipid shell-polymer core microparticles, it is proposed that microparticles according to the present invention presented will act as novel drug carriers with a wide range of applications, such as combinational therapy, oral delivery of poorly water soluble drugs and targeted delivery.

Example 2

Polymer-Lipid Hybrid (PLH) and Polymer-Lipid-Cryoprotectant Hybrid (PLCH) Microparticle-Based Compositions for Cinnarizine Materials and Methods The poorly water soluble, anti-emetic drug, cinnarizine (CIN) (Sigma-Aldrich Co. LLC, St Louis, Mo., United States of America), was loaded into both the lipid droplets and polymer nanoparticles of PLH and PLCH microparticles prepared according to the method described in Example 1, but wherein cinnarizine was dissolved in the lipid preparation (ie Miglyol® 812 or a preparation of long chain length triglycerides (LCT), soybean oil) at a concentration of 5% and in the PLGA/ethyl acetate solution (with PVA or DMAB) at a concentration of 5%. The PLGA used in these experiments were either of low molecular weight (ie. MW=7000-17000 Da) or high molecular weight (ie. MW=30000-60000). Where included, the cryoprotectant used was mannitol. Various dissolution studies were conducted according to standard protocols to assess the release of the cinnarizine from the PLH and PLCH microparticle compositions. A submicron MCT emulsion, stabilised by lecithin, with a droplet size of approximately 180 nm, a PLGA nanoparticle preparation and pure CIN were used for comparison.

Results and Discussion

Figure 9A:
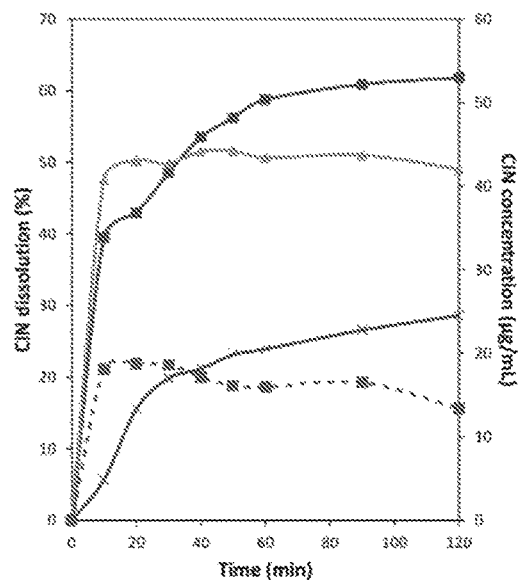
FIG. 9 provides graphical results for the release of the poorly water soluble drug, cinnarizine (CIN), as a function of time for: (A) (■) negatively charged PLCH microparticles, (▲) a submicron emulsion, (X) negatively charged PLGA-1 nanoparticles, and (※ with dashed line) pure CIN drug, in 0.1% SLS S0krd0TL and (B) a two-step dissolution for (■) negatively charged PLCH microparticles, (▲) negatively charged PLGA nanoparticles, and (♦) pure drug, in simulated gastric conditions (≤60 min) and simulated intestinal conditions (≥60 min)
Figure 9B:
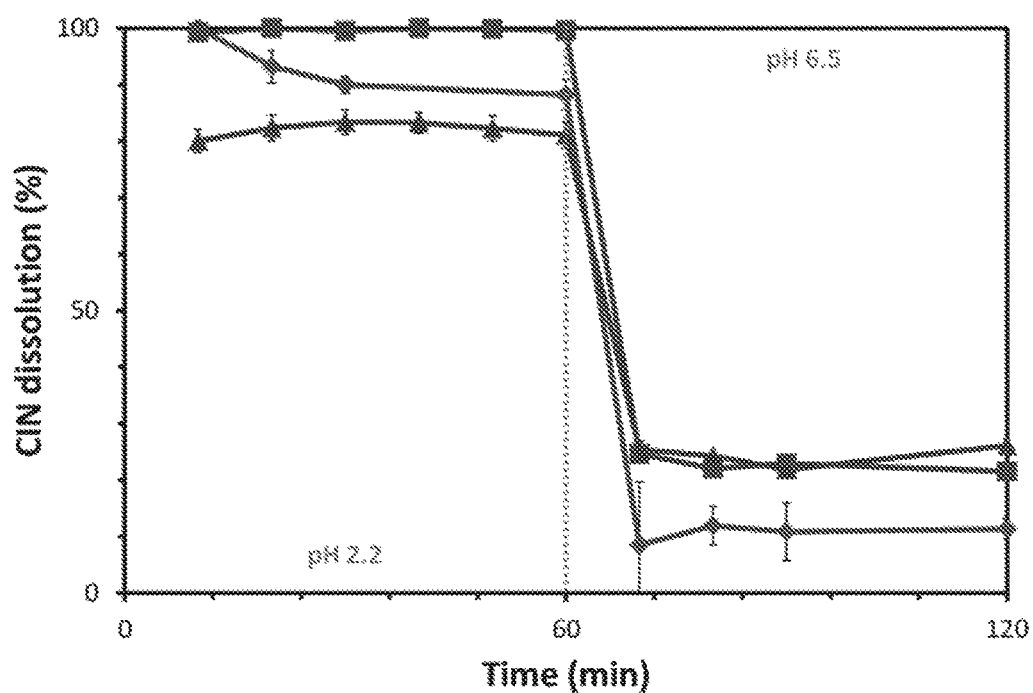

CIN release (ie. dissolution) into 0.1% sodium lauryl sulfate (SLS) solution was followed over 120 minutes. It was clearly apparent that CIN release from a PLCH microparticle composition (including high molecular weight PLGA) was enhanced compared to the emulsion alone, PLGA-1 nanoparticles and pure CIN (see FIG. 9A). Similar enhancement of CIN release was obsessed from the PLCH microparticle composition when assessed in simulated gastric conditions, and simulated intestinal conditions during a two-step dissolution (ie. 0-60 mins in the simulated gastric conditions and 60-120 minutes in the simulated intestinal conditions) (see FIG. 9B).

Figure 10:
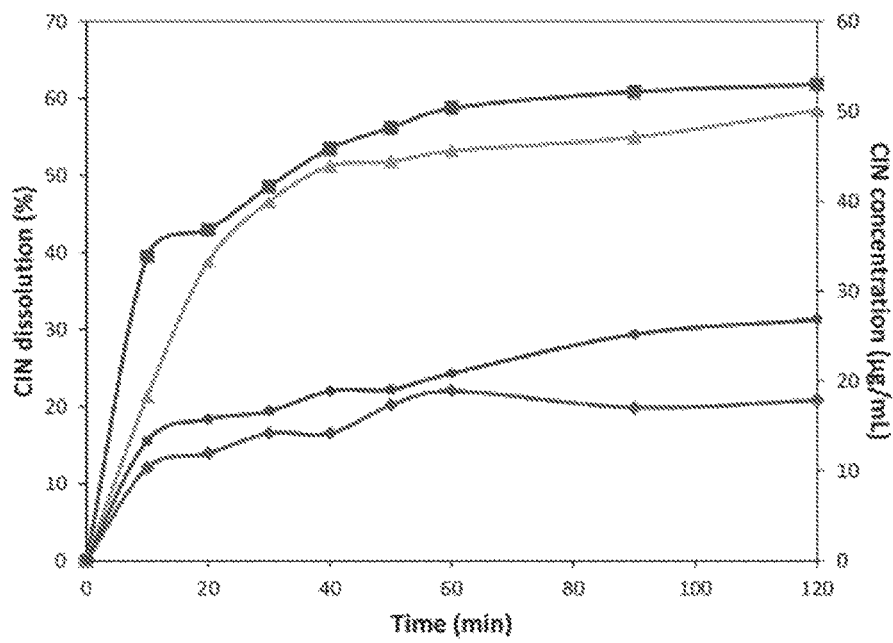
FIG. 10 provides further graphical results for the release of CIN into 0.1% SLS solution, showing the effect of charge on PLH/PLCH microparticle compositions as well as the presence of the cryoprotectant, mannitol, in the PLCH microparticles: (■) negatively charged PLCH microparticles, (▲) positively charged PLCH microparticles, (●) negatively charged PLH microparticles and (♦) positively charged PLH microparticles, and FIG. 11 provides graphical results of the release of CIN into 0.1% SLS solution, which show the effect of substituting high molecular weight PLGA with low molecular weight PLGA. The compositions used in these studies were negatively charged PLCH microparticles with (■) high molecular weight PLGA (MW=30000-60000) and (▲) low molecular weight PLGA (MW=7000-17000)

In further studies of release into 0.1% SLS, it was found that the rate and extent of CIN dissolution was greater for negatively charged microparticle compositions (ie including high molecular weight PLGA-1 nanoparticles) compared to positively charged microparticle compositions (including high molecular weight PLGA-2 nanoparticles) (see FIG. 10), which may be due to enhanced redispersion of anionic microparticles compared to cationic microparticles. In addition, it was found that the presence of mannitol within the PLCH microparticles facilitated more rapid release kinetics due to increased microparticle redispersibility (see FIG. 10).

Figure 11:
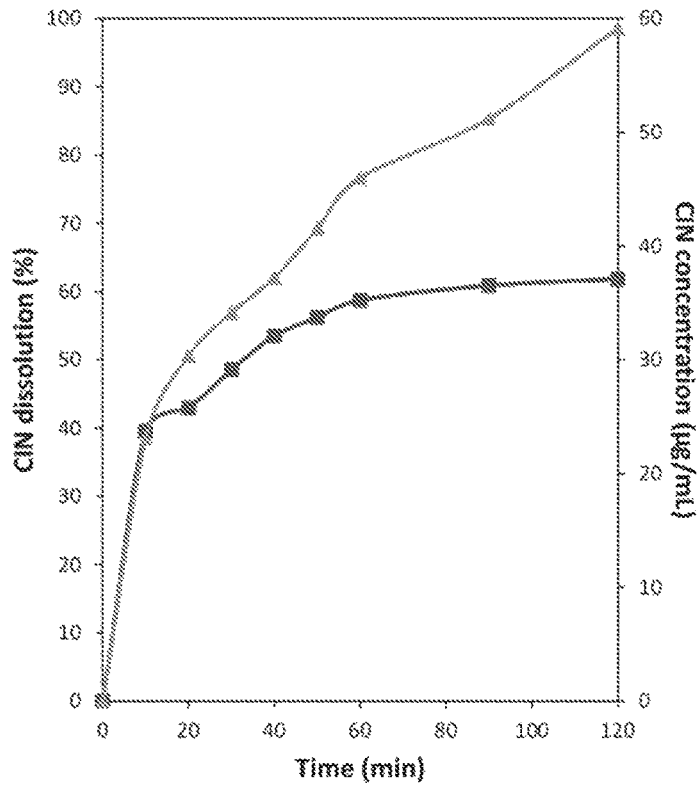
Figure 12:
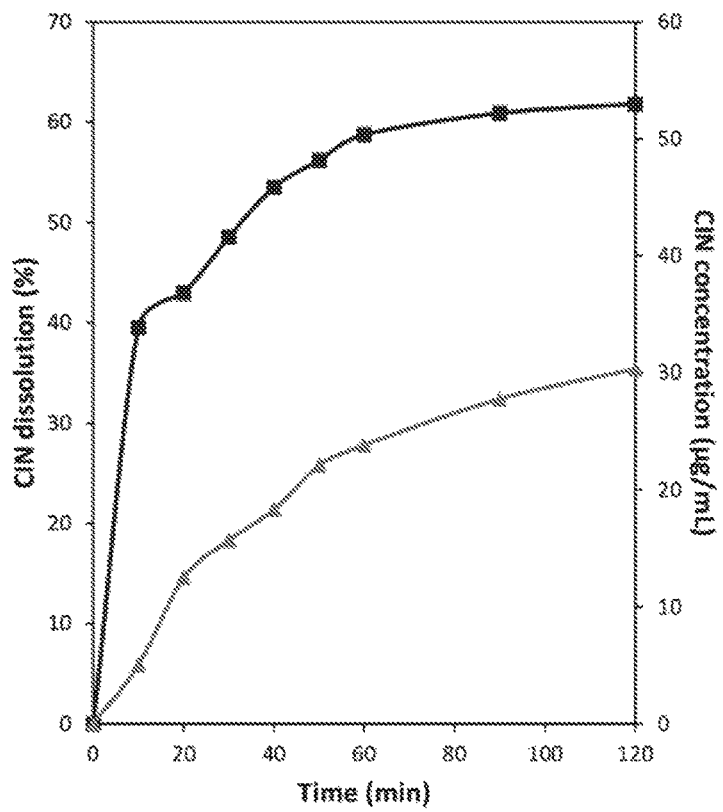
FIG. 12 provides the results of a CIN release study into 0.1% SLS solution, showing the effect of substituting medium chain length triglycerides (MCT) in the compositions with long chain length triglycerides (LCT). The compositions used in these studies were negatively charged PLCH microparticles formulated with (■) MCT and (▲) LCT.

In addition, it was observed that the release kinetics of CIN were enhanced when low molecular weight (MW=7000-17000) PLGA was used to formulate PLCH microparticles compared to high molecular weight PLGA (FIG. 11), demonstrating the case in which drug release can be controlled in PLH/PLCH microparticles. CIN release kinetics are also greatly affected by substituting MCT lipid with long chain length triglycerides (LCT) (see FIG. 12). In this case, LCT caused a decrease in CIN release from PLCH microparticle composition.

Example 3

Polymer-Lipid Hybrid (PLH) Microparticle-Based Composition for Cinnarizine

Figure 13:
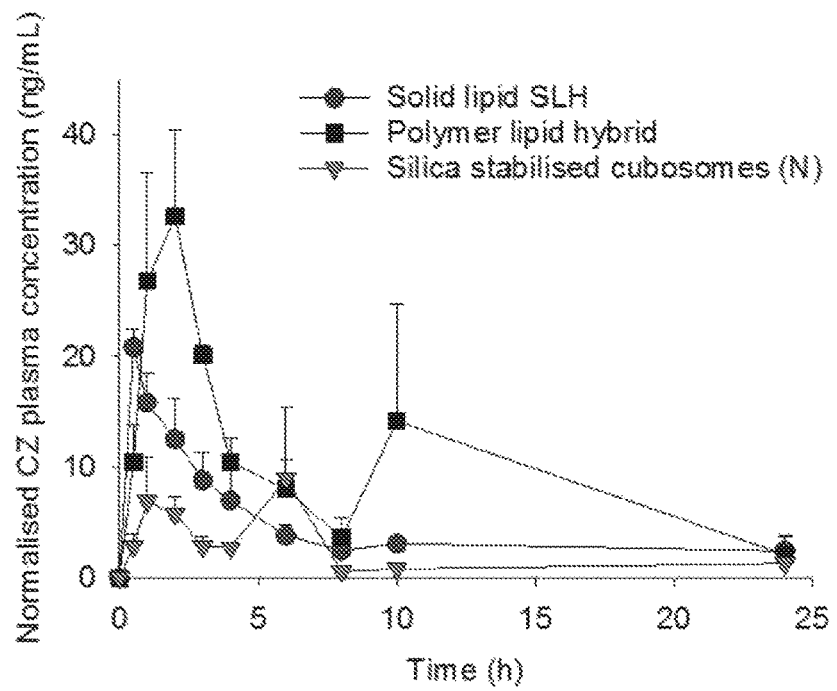
FIG. 13 provides the pharmacokinetic profiles of CIN from a PLH microparticle-based composition against comparative silica-containing lipid compositions: PLH (■), silica-lipid hybrid microparticle composition (●), and silica-stabilised cubosames (▼) over 24 h. Doses were normalised to 10 mg/kg, and plotted as mean plasma concentration ±SEM, n=4.

The pharmacokinetic behaviour of a PLH microparticle-based composition for cinnarizine (CIN) was investigated against comparative silica-containing compositions.
Materials and Methods
  Composition Preparation
  A silica-lipid hybrid (SLH) composition comprising CIN was prepared in accordance with previously described methods [18-20]. 160 mg of the dried composition was pre weighed into the 10 mL centrifuge tube, and then dispersed with 2 mL saline by vigorously vortexing the mixture. For a 300 g rat, 1.5 mL of this mix was dosed via oral gavage to rats for a dosage of 10 mg/kg. The CZ content was estimated to be about 1.5 wt %.
  A polymer-lipid hybrid (PLH) microparticle composition comprising CIN was prepared according to the method described in Example 1, but wherein cinnarizine was dissolved in the lipid preparation (ie Miglyol® 812). The PLGA was of low molecular weight (MW=7000-17000). The PLH composition was dosed into rats in a similar manner to that of the SLH composition, with 370 mg of dried composition weighed to allow for the same CZ content. A milky solution was formed upon hydration with 2 mL of saline.
  A silica-stabilised cubosomes (neutral) composition comprising CIN was prepared according to Bhatt et al, [44]. This composition was dosed into rats without further preparation at a lower CZ content (~0.5 wt. %). However, all PK concentrations were dose-normalised following Liquid Chromatography Mass Spectroscopy (LCMS) analysis.
  Surgical Procedures
  250-300 g male Sprague Dawley rats were used in this study. All formulations were conducted in quadruplicates (n=4). Surgical procedures were conducted as described by Nguyen et al. [42]. Briefly, rats, were anaesthetised via inhalation of isoflurane (5% v/v for induction, 2.5% v/v for maintenance) and weighed. The incision sites above the breast bone and the scruff were shaved, and analgesic (0.1 mL of Bupivacaine 0.5%) was subcutaneously injected. The right carotid artery was isolated and cannulated with a 0.96 mm×0.54 mm polyethylene tubing, with the cannula flushed with 2 IU heparin/saline solution. The rats were then attached to a harness/swivel system and placed in individual metabolism cages. Rats were also fasted and fed in the same manner as described by Nguyen et al. [42]. To allow for accurate determination of the dosed amount, the syringe and gavage were weighed before and after dosing rats. Blood sampling from the rats was performed at 0 h, 1 h, 2 h, 3 h, 4 h, 6 h, 8 h, 10 h and 24 h. A volume of 200 µL was drawn each time, then immediately dispensed into 1.5 mL centrifuge tubes pre-filled with 10 IU of heparin. To allow cannula patency, 2 IU of heparin saline solution was flushed through the cannula after each blood sampling. The blood samples were then centrifuged for 5 minutes at 7378×g. Plasma was collected as 2× aliquots of 50 µL and frozen at −20° C. until analysis.
  Plasma Extraction for CIN Content
  CIN plasma extraction was performed according to procedures described by Sahbaz et al. [43]. However, briefly, 50 µL blank plasma was spiked with cinnarizine and halofantrine (internal standards), with CIN standard concentrations of 5, 10, 25, 50, 100 and 250 ng/mL. Saturated ammonium sulphate was used to precipitate plasma protein, and then acetonitrile was added. Aliquots of 25 µL were collected from the supernatant, which was then transferred into vials for LCMS analysis.
  LCMS Analysis for CIN
  Processed plasma analysis was conducted on a single-quadrupole LCMS (Model 2010; Shimadzu Corporation, Kyoto, Japan), using methods and settings described by Sahbaz et al. [43].
Results and Discussion
  The results of this study are provided in Table 4 and in FIG. 13. The results indicate that the oral bioavailability of CIN was enhanced when encapsulated in PLH microparticles compared to two other hybrid microparticulate systems, given by greater AUC and $C_{max}$ values. The bioavailability of PLH is ~2.5 times that of the SLH composition and ~5 times that of the silica-stabilised cubosomes composition. Thus, the results highlight the promising release characteristics and solubilisation capacity of PLH/PLCH microparticles, whereby they may be used to increase the absorption of poorly water-soluble drugs. While not wishing to be bound by theory, this may be achieved by multiple delivery mechanisms; that is, lipid digestion and increased drug solubilisation in mixed micelles, slow release of drug from the PLGA nanoparticles into the GIT, and the potential for direct absorption of drug-containing PLGA nanoparticles (ie following microcapsule breakdown, which may be particularly suited for the administration of an active substance to the lung). The PLH/PLCH formulations may also be expected to extend the absorption half-life of an active substance, due to the release behaviour and drug delivery mechanisms.

TABLE 4

Pharmacokinetic parameters following oral administration of CIN incorporated in PLH, SLH and neutral silica-stabilised cubosome compositions. Doses were normalised to 10 mg/kg CIN administered to rats. Each data is expressed as the mean ± SEM, n = 4.

| Composition | $AUC_{0-t}$ last (ng/ml · h) | Mean $T_{max}$ (h) | Mean $C_{max}$ (ng/ml) |
|---|---|---|---|
| SLH | 108.6 ± 26.4 | 0.6 ± 0.1 | 20.8 ± 1.7 |
| PLH | 245.0 ± 77.5 | 4.0 ± 2.0 | 39.0 ± 7.3 |
| Silica-stabilised $V_2$ (N) | 54.3 ± 13.7 | 3.5 ± 1.4 | 14.7 ± 5.2 |

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgment of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

1. Raemdonck, K et al., *Chem Soc Rev* 43(1): 444-472 (2013).
2. Himami, B, *Int J Pharm Res dev* 3(1):59-75 (2011).
3. Jannin, V et al., *Adv Drug Deliv* 60(6):734-746 (2008).
4. Porter, C J H et al., *Adv Drug Deliv* 60(6):673-691 (2008).
5. Pouton, C W and C J H, Porter, *Adv Drug Deliv* 60(6): 625-637 (2008).
6. Simovic, S et al., *Nanoscale* 44:1220-1230 (2012).
7. Pillai, O and R Panchagnula, *Curr Opin Chem Biol* 5:447-451 (2001).
8. Italia, J L et al., *Pharm Res* 26(6):1324-1331 (2009).
9. Kumari, A et al., *Colloids and Surfaces B: Biointerfaces* 75(1): 1-18 (2010).
10. Kumbhar, D D and V B Pokharkar, *Colloids and Surfaces A: Physicochemical and Engineering Aspects* 436(0):714-725 (2013).
11. Liu, Y et al., *Int J Pharm* 395(1):243-25 (2010).
12. Mandal, B et al., *Nanomedicine* 9(4): 474-491 (2013).
13. Troutier, A-L et al., *Langmuir: the ACS journal of surfaces and colloids* 21(4):1305 (2005).
14. Thevenot, J et al., *J Phys Chem* 112(44):13812 (2008).
15. Thevenot, J et al., *Biomacromolecules* 8(11):3651 (2007).
16. Chu, C-H et al., *Nanotechnology* 22(18):185601 (2011).
17. Bala, I et al., *Crit Rev Therap Drug* 21(5):387-422 (2004).
18. Simovic, S et al., *Mol Pharm* 6(3):861-872 (2009).
19. Tan, A et al., *J Control Release* 134: 62-70 (2009).
20. Tan, A et al., *Angewandte Chemie International Edition* 51:5475-5479 (2012).
21. Simovic, S et al., *Phys Chem Chem Phys* 12:7162-7170 (2010).
22. Tan, A et al., *Mol Pharm* 7(2):522-532 (2010).
23. Tan, A et al., *Pharm Res* 28:2273-2287 (2011).
24. Simovic, S et al., *J Control Release* 143:367-373 (2010).
25. Joyce, P et al., *Langmuir* 30(10):2779 (2014).
26. Whitby, C P et al., *J Colloid Interface Sci* 375(1):142 (2012).
27. Harihan, S et al., *Pharm Res* 23(1):184-195 (2006).
28. Jang, D-J et al., *Eur J Pharm Sci* 28(5):405-411 (2006).
29. Sek, L et al., *J Pharmacol* 54(1):29-41 (2002).
30. Galindo-Rodriguez, S et al., *Physicochemical Parameters Associated with Nanoparticle Formation in the Salting-Out, Emulsification-Diffusion, and Nanoprecipitation Methods* 21(8):1428-1439 (2004).
31. Tomoda, K et al., *Preparation and properties of inhalable nanocomposite particles: Effects of the temperature at a spray-dryer inlet upon the properties of particles* 61(2):138-144 (2008).
32. Takashima, Y et al., *Int J Pharm* 343(1):262-269 (2007).
33. Vinarov, Z et al., *Langmuir: the ACS journal of surfaces and colfoids* 28(33):12140 (2012).
34. Mun, S et al., *Food Biophysics* 1(1):21-29 (2006).
35. Eydoux, C et al., *Biochemistry* 47(36):9553-9564 (2008).
36. Winkler, F K et al., *Nature* 343(6260):771-774 (1990).
37. Rao, J P and K E Geckeler, *Prog Polym Sci* 36:887-913 (2011).
38. Makadia, H K and S J Siegel, *Polymers* 3:1377-1397 (2011).
39. Crotts, G et al., *J Microencapsul* 15:699-713 (1998).
40. Labiris, N R and M B Dolovic, *Br J Clin Pharmacol* 56:588-599 (2003).
41. Vert, M et al., *Pure Appl Chem* 84:377-410 (2012).
42. Nguyen, T-H et al., *J Control Release* 153:180-186 (2011).
43. Sabbaz, Y et al., *Mol Pharm* 12:1980-1991 (2015).
44. Bhatt, A et al., *Curr Drug Deliv* 12:47-55 (2015).
45. Rao, S and C A Prestidge, *Exp Opin Drug Deliv* February 23:1-17 (2016).

The invention claimed is:

1. A dry composition comprising three-dimensional porous microparticles, wherein said microparticles comprise: (i) an active substance, (ii) polymeric nanoparticles, (iii) lipid droplets, (iv) a nanoparticle stabilising agent, and (v) a cryoprotectant; wherein said active substance is carried by said nanoparticles and/or lipid droplets; wherein the composition comprising 1 to 5 wt % of the active substance, 25 to 50 wt % of the polymeric nanoparticles, 25 to 50 wt % of lipid droplets, 1 to 25 wt % of the nanoparticle stabilising agent, and 1 to 10 wt % of the cryoprotectant based on the total weight of the composition; wherein the cryoprotectant is selected from the group consisting mannitol, lactose, trehalose, sucrose, glucose, fructose and sorbitol.

2. The composition of claim 1, wherein the active substance is a pharmaceutical agent.

3. The composition of claim 2, wherein the pharmaceutical agent is a poorly water soluble drug.

4. The composition of claim 1, wherein the polymeric nanoparticles comprise a biocompatible and/or biodegradable polymer.

5. The composition of claim 4, wherein the polymeric nanoparticles comprise a PLGA polymer.

6. The composition of claim 1, wherein the lipid droplets comprise a medium chain triglyceride (MCT).

7. The composition of claim 1, wherein the nanoparticle stabilising agent is selected from poly vinyl alcohol (PVA) and didodecyldimethyl ammonium bromide (DMAB).

8. The composition of claim 1, wherein the microparticles do not consist of a lipid shell-polymer nanoparticle core architecture.

9. The composition of claim 1 produced by a method comprising spray drying an oil in water (o/w) emulsion comprising lipid droplets and polymeric nanoparticles in the aqueous phase.

10. The composition of claim 1, wherein the microparticles have an average diameter of <5 μm.

* * * * *